United States Patent
Cragoe, Jr. et al.

(10) Patent No.: US 6,251,898 B1
(45) Date of Patent: Jun. 26, 2001

(54) MEDICAL USE OF FLUORENONE DERIVATIVES FOR TREATING AND PREVENTING BRAIN AND SPINAL INJURY

(75) Inventors: Edward J. Cragoe, Jr., Nacogdoches, TX (US); Paul J. Marangos, La Costa; Torsten R. Weimann, Cardiff by the Sea, both of CA (US)

(73) Assignee: Questcor Pharmaceuticals, Inc., Hayward, CA (US)

( * ) Notice: Subject to any disclaimer, the term of this patent is extended or adjusted under 35 U.S.C. 154(b) by 0 days.

(21) Appl. No.: 09/379,656

(22) Filed: Aug. 24, 1999

(51) Int. Cl.[7] .................. A61K 31/535; A61K 31/42; A61K 31/425; A61K 31/435; A61K 31/415

(52) U.S. Cl. .................. 514/228.8; 514/374; 514/365; 514/277; 514/400

(58) Field of Search .................. 544/88; 514/228.8, 514/365, 345, 277, 400, 374; 548/146; 546/302

(56) References Cited

U.S. PATENT DOCUMENTS

| | | |
|---|---|---|
| 4,316,043 | 2/1982 | Cragoe et al. . |
| 4,317,922 | 3/1982 | Cragoe et al. . |
| 4,337,354 | 6/1982 | Cragoe et al. . |
| 4,356,313 | 10/1982 | Cragoe et al. . |
| 4,356,314 | 10/1982 | Cragoe et al. . |
| 4,604,396 * | 8/1986 | Cragoe et al. . |
| 4,675,341 | 6/1987 | Cragoe . |
| 4,731,470 | 3/1988 | Pietruszkiewicz et al. . |
| 4,731,471 | 3/1988 | Cragoe et al. . |
| 4,731,472 | 3/1988 | Pietruszkiewicz et al. . |
| 4,769,370 | 9/1988 | Woltersdorf et al. . |
| 4,777,281 | 10/1988 | Woltersdorf et al. . |
| 4,782,073 | 11/1988 | Cragoe . |
| 4,797,391 | 1/1989 | Woltersdorf et al. . |

OTHER PUBLICATIONS

Cragoe, E.J., "Agents for the treatment of brain edema 2: [(2,3,9,9a–Tetrahydro–3–oxo–9a–substituted–1H–fluoren–7–yl)oxy]–alkanoic acids and some of their analogues," *J Med Chem* 29: 825–41 (1986).

Cragoe, E.J., "Drugs for the treatment of traumatic brain injury," *Medical Res Rev* 7: 271–305 (1987).

* cited by examiner

*Primary Examiner*—John Kight
*Assistant Examiner*—Binta Robinson
(74) *Attorney, Agent, or Firm*—Pennie & Edmonds LLP

(57) ABSTRACT

Newly-created fluorenone drugs can be used to prevent, treat, or otherwise reduce damage to a brain or spinal cord following a medical crisis. These new drugs are markedly improved analogs of previously-known fluorenone compounds that were never commercialized or developed into medically useful treatments. The new analogs have the following structure:

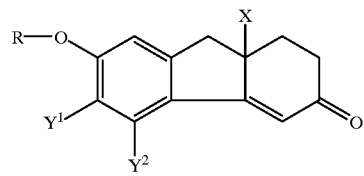

where X is a lower alkyl, substituted alkyl, or cycloalkyl group, R is selected from certain types of ether, ester, or amide groups, and $Y^1$ and $Y^2$ are halogen, hydrogen, or methyl. These new compounds can penetrate a blood-brain barrier and potently inhibit the unwanted release of excitotoxic neurotransmitters by astrocyte cells following an injury or insult to the brain or spinal cord. As an illustration, some of these new analogs were more than 30 times more potent than the previously known best compound in reducing aspartate release by stressed astrocytes. The new analogs also reduce swelling in astrocytes, thereby promoting proper blood flow through the brain and spinal cord following an injury or other crisis. These new analogs have been shown to work with very good efficacy in in vivo animal models of focal or global brain ischemia.

9 Claims, 13 Drawing Sheets

"Method E" Synthesis, Ether Product

GERI-E12

Synthesis of Ester Products

Method A

Hydroxy compound [2]

DMAP, pyridine

Anhydride with $R^2$ groups

Method B

Carboxylic acid with $R^2$ group

CDI

Hydroxy compound [2]

Ester product with $R^2$ group

| R group on #7 carbon | Compound number | Synthesis method |
|---|---|---|
| HO-CH₂-C(=O)- | L-644,711 (benchmark) | Prior art |
| (HO)₃C-CH₂- (tris(hydroxymethyl)methyl) | GERI-E1 | Example 1 |
| H₂N-CH₂-CH₂- | GERI-E2 | Example 2 |
| 2-(NaOOC)C₆H₄-CH₂- | GERI-E3 | Example 3 |
| 3-(NaOOC)C₆H₄-CH₂- | GERI-E4 | Example 4 |
| 4-(NaOOC)C₆H₄-CH₂- | GERI-E5 | Example 5 |
| 4-(oxazolinyl)C₆H₄-CH₂- | GERI-E6 | Example 6 |
| (oxazolinyl)-CH₂- | GERI-E7 | Example 7 |

| R group on #7 carbon | Compound number | Synthesis method |
|---|---|---|
| HO-CH₂-C(=O)- | L-644,711 (benchmark) | Prior art |
| (oxazoline)-CH₂- 9a group is hydroxyethyl | GERI-E8 | Example 8 |
| (thiazoline)-CH₂- | GERI-E9 | Example 9 |
| (oxazine)-CH₂- | GERI-E10 | Example 10 |
| (oxazoline)-CH₂-CH₂- | GERI-E11 | Example 11 |
| (thiophene)-CH₂-CH₂- | GERI-E12 | Example 12 |
| CH₃-C(=O)-O-CH₂- | GERI-E13 | Example 13 |
| (pyridine)-CH₂- | GERI-E14 | Example 14 |

| R group on #7 carbon | Compound number | Synthesis method |
|---|---|---|
| HO-C(=O)-CH₂-O— | L-644,711 (benchmark) | Prior art |
| CH₃-C(=O)-O— | GERI-Est1 | Example 15 |
| (H₃C)₂N-CH₂-C(=O)-O— | GERI-Est2 | Example 16 |

Ester products

| R group | Compound number | Synthesis method |
|---|---|---|
| HO-C(O)-CH₂- | L-644,711 (prior art, benchmark) | Prior art |
| MeO-CH(OMe)-CH₂-NH-C(O)-CH₂- | GERI-AmE1 | Example 17 |
| N≡C-CH₂-NH-C(O)-CH₂- | GERI-AmE2 | Example 18 |
| Ph-CH₂-NH-C(O)-CH₂- | GERI-AmE3 | Example 19 |
| (2-pyridyl)-CH₂-NH-C(O)-CH₂- | GERI-AmE4 | Example 20 |
| (imidazol-1-yl)-(CH₂)₃-NH-C(O)-CH₂- | GERI-AmE5 | Example 21 |
| (4,5-dihydrooxazol-2-yl)-CH₂-N(CH₃)-C(O)-CH₂- | GERI-AmE6 | Example 22 |

MEDICAL USE OF FLUORENONE DERIVATIVES FOR TREATING AND PREVENTING BRAIN AND SPINAL INJURY

GOVERNMENT SUPPORT

The research described herein was funded in part by the National Institutes of Health, under grant number 1R43NS35385-01A1. Accordingly, the federal government has certain rights in this invention.

RELATED APPLICATION

This application is being filed simultaneously with a related application entitled, "Fluorenone Compounds with Modified 7-Position Substituents for Treating and Preventing Brain and Spinal Injury", application Ser. No. 09/379, 816. It describes and claims various fluorenone derivatives with ether, ester, or amide groups bonded to the 7-position of the fluorenone structure. The contents of that application are incorporated herein by reference, as though fully set forth herein.

BACKGROUND OF THE INVENTION

This invention is in the fields of neurology and pharmacology, and relates to drugs that can minimize brain injury due to various causes, such as traumatic head injury or crises such as stroke, cardiac arrest, or asphyxiation.

The compounds disclosed herein (referred to as "fluorenone" drugs) are all within a class of compounds that were first discovered, and recognized to be potentially useful for reducing brain damage, in the 1970's. A great deal of time, effort, and expense were devoted to these drugs, and they were extensively patented and studied by one of the world's largest pharmaceutical companies, Merck & Company, Inc.

However, these drugs were never commercialized in any way, at any time, by Merck or any other company. The primary discoverer and inventor, Dr. Edward Cragoe, Jr., retired from Merck years ago, without ever getting to see any of these drugs provide the much-needed public service of offering a treatment to reduce or prevent brain injury. The patents on these fluorenone drugs have either expired, or were deliberately allowed to lapse due to intentional nonpayment of the maintenance fees. The expired or lapsed patents in this field which cover fluorenone compounds include U.S. Pat. Nos. 4,316,043 (issued in February 1982); 4,317,922 (March 1982); 4,337,354 (June 1982); 4,356,313 and 4,356,314 (both in October 1982); 4,604,396 (August 1986); 4,675,341 (June 1987); 4,731,471 and 4,731,472 (both in March 1988); 4,782,073 (November 1988); 4,797,391 (January 1989); and 4,835,313 (May 1989).

Other lapsed and abandoned US patents which disclose and claim methods of synthesizing such compounds include U.S. Pat. Nos. 4,605,760 and 4,605,761 (both issued in August 1986).

Still other lapsed and abandoned US patents which disclose fluorenone-type compounds that are not as closely related to the subject matter of this invention include U.S. Pat. Nos. 4,731,470 (March 1988); 4,769,370 (September 1988); and 4,777,281 (October 1988).

Not a single one of the "fluorenone" compounds covered in any of the patents listed above has ever been commercialized or made available to the public. As mentioned above, all of the patents listed above were allowed to lapse and expire, due to nonpayment of their maintenance fees.

Fluorenone Compounds

The compounds disclosed in the most relevant prior art belong to a class of compounds that are analogs (mostly in the form of ether or ester analogs) of R-(+)-(5,6-dichloro-2,3,9,9a-tetrahydro-7-hydroxy-9a-hydrocarbyl-1H-fluoren-3-one compounds. Their general chemical structure is:

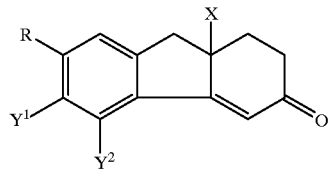

where R, X, and $Y^1$ and $Y^2$ are various organic moieties as specified in the prior art patents.

These compounds are sometimes called "fluorene" compounds or derivatives, because they are contain a tri-cyclic structure called fluorene, which is shown in the Merck Index and in various articles cited therein which date back to the 1920's. The illustration of fluorene analog L-644,711, shown at the top of FIG. 1 herein, shows the conventional numbering used for the carbon atoms in the three-ring structure of fluorene.

It should be noted that fluorene has no relation to fluorine (the halogen atom), even though both words are pronounced the same. To avoid confusion, a fluorene compound which bears a double-bonded oxygen attached to one of the three ring structures can be called a "fluorenone" compound. All of the drugs discussed herein are fluorenone compounds, since they bear a double-bonded oxygen attached to the 3-carbon atom, as shown in FIG. 1.

Cragoe et al 1986 and Cragoe 1987, which are review articles, provide additional information on prior art fluorenone compounds. Briefly, Cragoe and his coworkers initially began working with compounds known as "indanones", which were demonstrated to have diuretic activity (i.e., they caused the excretion of large quantities of body fluids, via urine); see Woltersdorf et al 1977 and deSolms et al 1978. By systemically reducing body fluids via increased urine output, some of these drugs were shown to help reduce edema inside the brain after a traumatic brain injury. This reduction of edema inside the brain helped restore blood flow in an injured brain, as discussed in Cragoe et al 1986.

It was subsequently discovered and shown that some indanone compounds (which are bi-cyclic) could be further cyclized to generate tri-cyclic fluorenone compounds, which had increased activity in reducing brain edema without the unwanted systemic side effects produced on body tissues by diuretic agents; this was discussed in Cragoe 1987.

Accordingly, subsequent research by the Merck scientists focused on the tri-cyclic fluorenone compounds as potential neuroprotective drugs. That research in the late 1980's eventually settled on the L-644,711 compound as Merck's lead compound for in vitro and in vivo testing, since it was one of the most desirably active, effective, and selective compounds known at that time. In that particular compound, the "X" group attached to the 9a-position is a propyl group in the R(+) orientation, and the "R" group attached to the 7-carbon atom is a carboxymethyl group ($HOOCCH_2$—). The complete chemical name of compound L-644,711 is R(+)-[(5,6-dichloro-2,3,9,9a-tetrahydro-3-oxo-9a-propyl-1H-fluoren-7-yl)oxy]acetic acid, and it is shown as a starting reagent at the top of FIG. 1. It is also shown as compound (+)-5c in Cragoe et al 1986 (which summarizes the steps used to synthesize the entire series of fluorenone compounds), and as compound B-3(+) in Cragoe 1987 (which discusses the biological activities of various fluorenone compounds).

Samples of L-644,711 were provided by the Merck company to various researchers at medical schools and elsewhere, who tested it and reported on its potential for preventing brain damage (see, e.g., Kimelberg et al 1987 and 1989; Barron et al 1988; Trachtman et al 1989; Bednar et al 1992; and Kohut et al 1992).

However, as noted above, that line of research was abandoned within a few years. It did not lead to any commercialized compounds, and all of the US patents listed above were allowed to lapse and expire, due to non-payment of their maintenance fees.

L-644,711 was used as a "benchmark" compound in the new research disclosed herein. This new research, which was sponsored and funded by Cypros Pharmaceutical Corporation (Carlsbad, Calif.), identified a number of compounds that are markedly better than L-644,711 as a neuroprotective drug, as measured by appropriate biological assays.

Accordingly, the new compounds disclosed herein should be regarded as highly improved fluorenone compounds which perform markedly better than any of the prior art compounds disclosed in any of the patents cited above, or in any other publications that are known to the Inventors herein.

Background on Glial Cells and Traumatic Brain Edema

Inside the mammalian central nervous system (CNS, which includes the brain and spinal cord), cells are divided into two major categories: neurons, and glial cells. Neurons are cells which actually receive and transmit nerve signals. By contrast, the term "glial cells" includes a variety of supporting cells which help nourish and protect neurons, but which do not and cannot receive and transmit nerve signals. Glial cells are subdivided into various cell types, including: (1) astrocytes, which have cell shapes that resemble a star in certain respects, with a main central portion having various arms projecting outwardly from the central portion; (2) oligodendrocytes, which have several long projecting "dendrites", which usually wrap around certain portions of the neurons, to provide myelin sheaths which surround neuronal dendrites and axons; and (3) microglial cells, which are migratory cells that are part of the immune system inside the brain, and which collect and break down waste products, dead cells, and bacterial cells and viruses inside the brain tissue.

More information on glial cells, and on the interactions between glial cells and neurons inside the central nervous system, is contained in numerous reference books on neurology, such as *Principles of Neural Science*, 3rd edition, by E. Kandel & J. Schwartz (Elsevier Publishing, New York, 1991), a one-volume textbook, or *Encyclopedia of Neuroscience*, edited by G. Adelman (Birkhauser Publishing, Boston, 1987), a multi-volume treatise.

For convenience, most of the remaining discussion focuses on the brain, and on injuries or other insults to the head. However, it should be understood that astrocytes and other glial cells also exist and function in essentially the same manner in a mammalian spinal cord. Accordingly, the drugs disclosed herein are believed to be useful for reducing neuronal damage to a spinal cord as well as to a brain, as further discussed below.

The drugs discussed herein may have various effects on any type of glial cells. Astrocyte cells were selected and used for various tests disclosed herein for a number of reasons, as follows.

Astrocyte cells often swell after a head injury, and this cellular swelling can severely aggravate and multiply the extent and severity of brain damage resulting from an injury. The complete set of causes and aggravating factors which lead or contribute to astrocyte swelling and edema are not totally understood; however, a sequence of three important cellular reactions are known to be major contributing factors.

In the first step in this series of reactions, chloride ions ($Cl^-$) begin entering astrocyte cells in abnormally large quantities by an active process, from surrounding extracellular fluids. These ions enter the cells through specialized chloride channels that pass through the astrocyte cell membranes.

In the second step, positively charged sodium ions ($Na^+$) also begin entering the astrocyte cells in abnormally large quantities by a passive process, due to effect of the excess of negatively charged $Cl^-$ ions inside the cells.

In the third step, after the influx of ions into astrocyte cells creates an osmotic imbalance between the intracellular and extracellular fluids, water molecules begin seeping into the astrocyte cells, in an effort to re-establish proper osmotic balances across the cell membranes.

As a result of these processes (and possibly other contributing factors as well), the affected astrocyte cells become swollen due to the presence of large quantities of excess water. The medical term for this condition is "edema", which refers to swelling of cells or tissue caused by a combination of (a) entry of too much fluid into the cells or tissue, combined with (b) an inability of the cells or tissue to excrete or otherwise properly manage the excess fluid.

When astrocyte cells become swollen, they begin pressing against the capillaries that provide blood to the brain tissue. Capillary walls inside the brain are very thin and pliable; this is necessary to allow adequate quantities of glucose, oxygen, and other nutrients to permeate out from the blood and through the capillary walls, to provide nourishment to nearby neurons and glial cells.

Because of their thinness, capillary walls cannot significantly resist the pressure that is generated when astrocyte cells become edematous. Accordingly, astrocyte edema can severely restrict subsequent blood flow through capillaries that serve an affected region inside the brain. This reduction of capillary blood flow through the brain can quickly become catastrophic, and will lead to severe and possibly lethal brain damage, unless it is relieved quickly.

Astrocyte cells can also severely aggravate brain damage after a head injury, due to a second major factor. This factor arises from the fact that in a healthy brain, astrocyte cells help to "mop up" excess quantities of certain types of excitatory neurotransmitters, especially glutamate and aspartate. In a healthy brain, glutamate and/or aspartate are released by a neuron in order to transmit a nerve impulse to an adjacent neurons. After being released into a synaptic junction, a glutamate or aspartate molecule briefly binds to a receptor protein on the surface of the signal-receiving neuron. This interaction between the glutamate or aspartate transmitter molecule and the neuronal receptor provokes a cellular response, which causes ion channels in the signal-receiving neuron to briefly open and allow certain types of ions to enter the neuron. This influx of ions changes the chemical state of the neuron, thereby activating ("depolarizing") the neuron, and causing it to release its own set of neurotransmitter molecules at synapses with other neurons.

As soon as a neuron has been activated (i.e., depolarized), it activates its ion pumps and begins pumping ions back out of the cell, in order to regain its polarized state so it will be ready to receive another nerve impulse. This effort to regain a polarized "ready-to-fire" state requires a neuron to expend substantial amounts of energy. In effect, the "resting state" of a neuron is on a high-energy plateau; it can reach a "ready-to-fire" resting state only by pumping out large quantities of ions.

When glutamate or aspartate are used to transmit a nerve impulse, the glutamate or aspartate molecules quickly disengage from the receptor proteins and enter the synaptic fluid again. In a healthy brain, the large majority of glutamate and aspartate molecules which have been released from neuronal receptors in this manner are quickly pumped back inside the neurons that released those transmitter molecules, by a cellular transport system which requires energy to run. However, some glutamate and aspartate molecules are not handled properly by this neuronal pumping system, and they diffuse out of the synaptic junctions, in a manner comparable to a slowly dripping faucet. These errant neurotransmitters would pose a serious risk of creating unwanted and possibly destructive nerve impulses, if they were not promptly managed by other mechanisms.

To prevent uncontrolled nerve signals from being triggered by glutamate and aspartate molecules which have gradually leaked out of the synaptic junctions between neurons, astrocyte cells have developed a highly useful "mopping up" function. In simple terms, astrocyte cells will grab any glutamate or aspartate molecules they encounter, and pump those molecules into their cell interiors. Because astrocyte cells do not quickly metabolize and degrade these neurotransmitter molecules, the astrocyte cells gradually accumulate fairly large quantities of glutamate and aspartate molecules.

In a healthy brain, this is good and proper; the glutamate and aspartate molecules which are stored inside astrocyte cells do not harm those cells in any way. However, if a brain injury occurs which is severe enough to cause badly-stressed astrocytes to swell and suffer from edema, the stressed astrocytes can begin releasing their stored-up quantities of glutamate and aspartate. If this occurs, the newly-released glutamate and aspartate will begin contacting neurons again, triggering unwanted nerve impulses in uncontrolled ways and at the worst possible time. The neurons will already be under severe stress due to the brain injury which triggered the crisis, and as mentioned above, each time a neuron undergoes a depolarizing event, it immediately begins expending large quantities of energy in an effort to pump out the ions that entered it when the neuron "fired", so it can get ready to receive the next nerve impulse.

Accordingly, if a traumatic brain injury causes astrocyte cells to swell and begin releasing glutamate and aspartate into extracellular fluids inside the brain, matters can quickly go from bad to worse. An "excitotoxic cascade" of cell damage and death inside the brain can break free of the restraining limits which the brain normally uses to prevent over-excitation. These processes can severely aggravate brain damage, and often lead to the death of the victim.

These processes, and the correlations between cellular swelling and the release of glutamate and aspartate inside CNS tissue, are discussed in articles such as Bourke et al 1983 and Kimelberg et al 1990.

The terms "excitotoxic" and "excitotoxin" are used by neurologists to indicate that excitatory neurotransmitters, which play an essential role in a healthy brain, can become deadly neurotoxins in a brain suffering from a crisis. During and after an ischemic, hypoxic, or similar crisis, glutamate and aspartate both become excitotoxins, and can kill affected neurons through toxic over-excitation.

Accordingly, this invention discloses new compounds which are more potent and effective than any previously known compounds in reducing the release of excitotoxic quantities of glutamate and aspartate by glial cells (including astrocyte cells) following a CNS crisis.

Since these new compounds exert this effect, they are referred to herein as "GERI" compounds, where GERI is the acronym for "Glial Excitotoxin Release Inhibitors". This activity has been shown using an assay involving the release of radiolabelled aspartate by osmotically-stressed astrocytoma cells, described in detail in Example 23, below.

Referring to these compounds as "Glial Excitotoxin Release Inhibitors" does not imply that their GERI function is their only known useful activity. A correlation was observed during the astrocyte assays, indicating that the potency of various fluorenone analogs in inhibiting excitotoxin release by stressed astrocyte cells apparently correlates with their ability to also reduce edematous swelling by the cells. This observation suggests that (i) the GERI class of fluorenone analogs may be extremely useful in preventing or reducing CNS damage caused by various types of crises as discussed below; and, (ii) the D-aspartate release assay may be useful as an easily measured, readily quantifiable indicator of a GERI compound's ability to minimize astrocyte swelling, and possibly relieve and reduce elevations in intracranial pressure as well, following a head trauma or other CNS crisis. If desired, such correlations can be further elucidated by quantitative measurements of edema in astrocytes, using in vitro assays such as described in O'Connor et al 1993.

Based on the assays done to date, which include in vivo animal tests as disclosed in Examples 24 and 25, the GERI compounds disclosed herein are believed to be effective and potent neuroprotective compounds, which can be used to reduce and prevent damage to a mammalian brain and/or spinal cord due to any of the following causes and etiologies:

1. physical trauma to the head or spinal cord, as can occur in automobile accidents, bad falls, sports injuries, etc.;
2. a brain concussion, which can occur due to physical trauma to the head, and in certain other types of situations involving rapid acceleration or deceleration of the head;
3. stroke, including ischemic stroke caused by thrombosis or embolism, regardless of where a blood clot or other embolus originates in the body;
4. other disruptions of proper blood flow through the brain, such as (i) cerebral hemorrhage; (ii) general circulatory failure or disruption, such as caused by cardiac arrest; (iii) hemodynamic shock, such as caused by loss of blood due to injury or hemorrhage elsewhere in the body; (iv) vasculatory damage, as can be caused by vascular disease, certain types of bacterial, viral, or other microbial infection, and other comparable causes; (v) cerebral or spinal tumors; and, (vi) glial cell swelling caused by infections (such as viral, bacterial, or other microbial meningitis, encephalitis, or encephalomyelitis, Reyes syndrome, or AIDS) or other mechanisms, such as hydrocephalus;
5. hypoxic injury to the brain (i.e., inadequate oxygen supply), which arises as a direct result of any ischemic crisis, and which can also be caused by respiratory disruption, as occurs during incipient drowning or suffocation, carbon monoxide poisoning, etc.; and,
6. post-operative brain injury or stress, as can be caused by neurosurgery, or by cardiopulmonary bypass for a prolonged period.

Accordingly, one object of this invention is to disclose new drugs which can reduce and minimize brain and spinal damage following traumatic injuries.

Another object of this invention is to disclose new drugs which can reduce and minimize brain damage following various types of medical crises, such as strokes, cardiac arrest, and infective or inflammatory processes such as meningitis, encephalitis, or encephalomyelitis.

Another object of this invention is to disclose a class of drugs which can minimize astrocyte swelling inside the brain, following an injury or infection that affects the head or central nervous system.

Another object of this invention is to disclose a class of drugs which can be used to minimize the release, by astrocyte cells, of excitatory neurotransmitters (especially glutamate and aspartate) inside the brain or spinal cord after a head or spinal injury.

In addition, another object of this invention is to disclose certain drugs that can markedly outperform and improve upon L-644,711, a preferred compound from the "fluorenone" class of drugs which was extensively studied but never commercialized or made available to the public. Thus, the compounds of this invention possess greater potency for the treatment of brain and spinal cord injury, and they also enjoy a broad scope of biochemical mechanism of action.

These and other objects of the invention will become more apparent through the following summary, drawings, and description of the preferred embodiments.

BRIEF SUMMARY OF THE INVENTION

Newly-created fluorenone drugs can be used to prevent, treat, or otherwise reduce damage to the brain or spinal cord of a human patient suffering a medical crisis. These newly created drugs are markedly improved analogs or derivatives of certain previously-known fluorenone compounds that were never commercialized or developed into medically useful treatments. The new analogs have the following general structure:

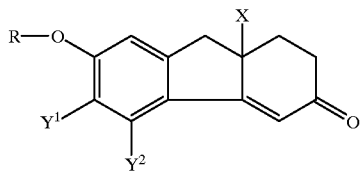

where X is a lower alkyl, substituted alkyl, or cycloalkyl group, R is selected from certain types of ether, ester, or amide groups, and $Y^1$ and $Y^2$ are halogen, hydrogen, or methyl. These new compounds can penetrate a mammalian blood-brain barrier and potently inhibit the unwanted release of excitotoxins by astrocyte cells following a head injury, stroke, cardiac arrest, or other CNS crisis. As an illustration, some of the newly created analogs were more than 30 times more potent than the previously known best compound in reducing aspartate release by stressed astrocyte cells. The new analogs can also help reduce swelling in astrocyte cells, and can thereby help reduce brain damage and promote proper blood flow through the brain following a head injury or other crisis. These new analogs have been shown to work with very good efficacy in in vivo animal models of both global and focal brain ischemia. Accordingly, these compounds can reduce brain or spinal cord damage caused by a hypoxic, ischemic, infective, inflammatory, or other injury, crisis, or insult to the brain or spinal cord.

DETAILED DESCRIPTION OF THE INVENTION

Figure 1:
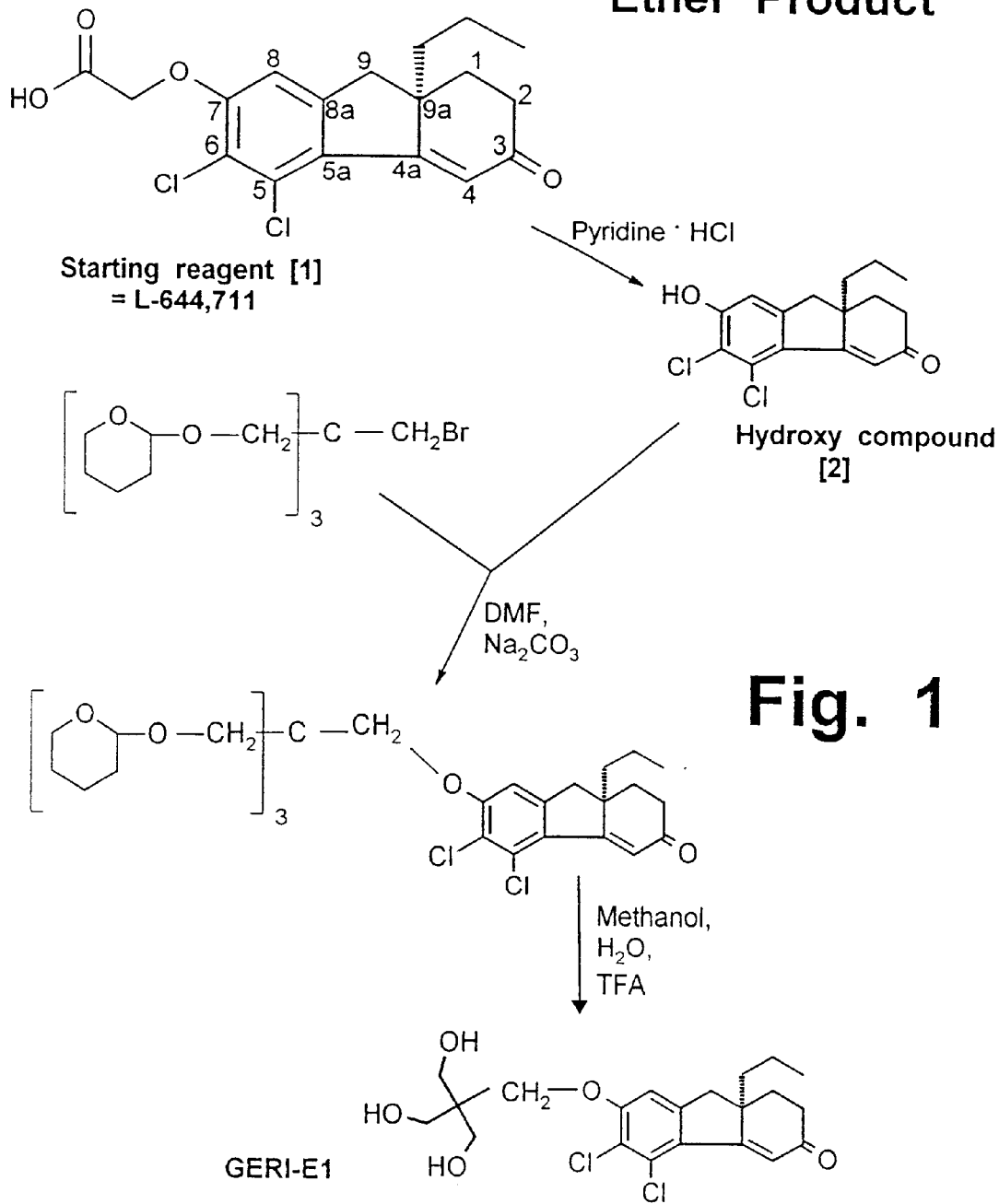
FIG. 1 depicts a "Method A" synthetic pathway used to prepare GERI-E1, a fluorenone ether analog with improved biological activity, using a brominated intermediate. This synthesis is described in detail in Example 1.

The compounds of the instant invention are conveniently characterized by reference to the following structural formula:

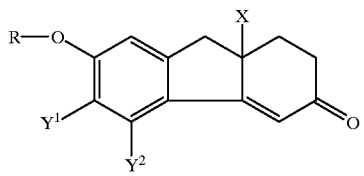

wherein X is lower alkyl, such as methyl, ethyl, propyl, isopropyl, and the like; lower cycloalkyl, such as cyclopropyl, cyclobutyl, cyclopentyl, and the like; and substituted lower alkyl, such as 2-hydroxyethyl, chloroethyl, trifluoromethyl, and the like.

R is selected from among $R^1$ groups which consist of substituted alkyl such as hydroxyalkyl, polyhydroxyalkyl, di(hydroxyalkyl)alkyl, tri(hydroxyalkyl)alkyl, alkoxyalkyl, dialkoxyalkyl, haloalkyl, aminoalkyl, alkylaminoalkyl, dialkylalkyl, substituted alkylamino such as hydroxyalkylaminoalkyl, di(substituted-alkylamino)alkyl such as di(hydroxyalkyl)aminoalkyl; aryl or substituted aryl groups, wherein the aryl group may be substituted by halo, carboxy, amino, alkyl, alkoxy, alkoxycarbonyl, or alkanoyl groups; and aralkyl groups, wherein the alkyl group can be lower alkyl and wherein the aryl group may be substituted as above; heterocyclic, substituted heterocyclic and heterocyclic-alkyl or substituted-heterocyclic-alkyl wherein, in each instance, the heterocyclic group is a 2-oxazolinyl or substituted 2-oxazolinyl group, 2-thiazolinyl or substituted 2-thiazolinyl group, 2-(tetrahydro-1,3-oxazinyl) group, 2-(tetrahydro-1,3-thiazolinyl) group, and the like; lower alkanoyloxyalkyl, and substituted alkanoyloxyalkyl.

R may also be alkanoyl or substituted alkanoyl which can be represented by $R^2$—C(O)— wherein $R^2$ is alkyl or substituted alkyl where the substituent is alkoxy, dialkylamino and the like.

R may also be represented by $R^3R^4NC(O)CH_2$— where $R^3$ can be alkyl (unbranched, branched, unsubstituted) or substituted alkyl wherein the substituent is: amino, dialkylamino, guanidino, hydroxy (such as where $R^3$-alkyl is 2,2-di(hydroxymethyl)propyl or 2,2-di(hydroxymethyl)-3-hydroxypropyl), alkoxy (such as where $R^3$-alkyl is 2,2-di(methoxy)ethyl, 2,2-di(ethoxy)ethyl, or 3,3-di(methoxy)propyl), aryl or substituted aryl (such as where $R^3$-alkyl is benzyl, phenethyl, chlorobenzyl, methoxybenzyl, ethoxybenzyl, aminobenzyl, hydroxybenzyl, carboxybenzyl, acetylbenzyl, methylbenzyl, 2-phenylpropyl or 1-phenylethyl, and the like); heterocyclic, wherein $R^3$-alkyl is a group such as 2-pyridylmethyl, 3-pyridylmethyl, 4-pyridylmethyl, 1-imidazolylpropyl, 3-hydroxy-5-isoxazolylmethyl, 2-pyrimidylmethyl, 2-pyrrolidinylmethyl, 2-pyrazinylmethyl, 2-tetrahydropyrimidylmethyl, 2-(tetrahydro-1,3-oxazinyl) methyl, 2-thiazolylmethyl, or 2-oxazolinylmethyl.

In such compounds $R^4$ can be hydrogen, a lower alkyl group, such as a methyl or ethyl group; or generally any other group such as amino which does not generate steric hindrance or interference when coupled to the nitrogen atom along with the $R^3$ group.

The 5-position and 6-position substituents, represented by $Y^1$ and $Y^2$, can be halogen, hydrogen, or methyl. Especially preferred are 5,6-dichloro compounds, as illustrated above and in the drawings. Other halogen, hydrogen, or methyl substituents can be incorporated at these positions by methods disclosed in the prior art cited above, or by other methods known to those skilled in the art.

It should be noted that the 9a-carbon atom (to which the X-substituent is attached) is chiral, and therefore the compounds of the invention may be racemic. However, these compounds or their precursors can be resolved so that the pure or essentially pure enantiomers can be prepared, thus the invention includes the pure or essentially pure enantiomers. This is an important point since some of the racemates possess one enantiomer which is much more active than the other one. Furthermore, the less active enantiomer may possess some level of toxicity, and may depress or interfere with the inhibitory action of the more active enantiomer at the tissue level. Thus, it is often advantageous to use a single active enantiomer rather than the racemate. In many instances the R(+) is the more active enantiomer (i.e. compounds in which X is ethyl or propyl) by a wide margin. In other instances, the more biologically active enantiomer may be the (−) configuration (e.g., where X is cyclopentyl), and the margin of difference in the biological activity of the two enantiomers may be considerably more narrow.

The preferred embodiments of the instant invention are realized in the following structural formula

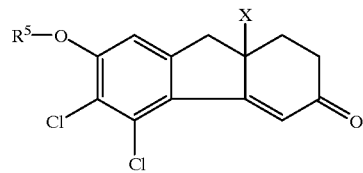

wherein X is as described above, and $R^5$ is dimethylaminoalkyl, hydroxyalkyl, polyhydroxyalkyl, substituted aralkyl, heterocyclic-alkyl, alkanoyl, substituted alkanoyl, alkanoyloxyalkyl, or substituted alkanoyloxyalkyl.

$R^5$ may also be represented by $R^6R^7NC(O)CH_2$— wherein $R^6$ is alkyl, hydroxyalkyl, dialkoxyalkyl, aralkyl, substituted aralkyl, or heterocyclic-alkyl, and $R^7$ is H or lower alkyl or hydroxyalkyl. Also included are the enantiomers of each racemate, and the corresponding esters and salts.

Also preferred is R(+)-5,6-dichloro-7-[3-hydroxy-2,2-bis-(hydroxymethyl)propyloxy]-9a-propyl-2,3,9,9a-tetrahydro-1H-fluoren-3-one, and the corresponding esters.

Also preferred is R(+)-5,6-dichloro-2,3,9,9a-tetrahydro-(2-aminoethyl)-9a-propyl-1H-fluoren-3-one, and the corresponding salts.

Also preferred are R(+)-2-[(5,6-dichloro-2,3,9,9a-tetrahydro-3-oxo-9a-propyl-1H-fluoren-7-yl)oxymethyl] benzoic acid, and the corresponding esters and salts.

Also preferred are R(+)-3-[(5,6-dichloro-2,3,9,9a-tetrahydro-3-oxo-9a-propyl-1H-fluoren-7-yl)oxymethyl] benzoic acid, and the corresponding esters and salts.

Also preferred are R(+)-4-[5,6-dichloro-2,3,9,9a-tetrahydro-3-oxo-9a-propyl-1H-fluoren-7-yl)oxymethyl] benzoic acid, and the corresponding esters and salts.

Also preferred are R(+)-5,6-dichloro-2,3,9,9a-tetrahydro-7-[4-(2-oxazolinyl)phenylmethoxy]-9a-propyl-1H-fluoren-3-one, and the two isomeric compounds, R(+)-5,6-dichloro-2,3,9,9a-tetrahydro-7-[2-(2-oxazolinyl)phenylmethoxy]-9a-propyl-1H-fluoren-3-one and R(+)-5,6-dichloro-2,3,9,9a-tetrahydro-7-[3-(2-oxazolinyl)phenylmethoxy]-9a-propyl-1H-fluoren-3-one, and the corresponding salts of each compound.

Also preferred are R-(+)-2-{[(5,6-dichloro-2,3,9,9a-tetrahydro-3-oxo-9a-propyl-1H-fluoren-7-yl)oxy]methyl}-oxazoline and the corresponding salts.

Also preferred is (±)-2-{[5,6-dichloro-2,3,9,9a-tetrahydro-3-oxo-9a-(2-hydroxyethyl)-1H-fluoren-7-yl)oxy]-methyl}oxazoline, its R(+) enantiomer, and the corresponding salts.

Also preferred are R(+)-2-{[5,6-dichloro-2,3,9,9a-tetrahydro-3-oxo-9a-propyl-1H-fluoren-7-yl)oxy]methyl}-thiazoline, and the corresponding salts.

Also preferred are R(+)-2-{[5,6-dichloro-2,3,9,9a-tetrahydro-3-oxo-9a-propyl-1H-fluoren-7-yl)oxy]methyl}-tetrahydro-1,3-oxazine, and the corresponding salts.

Also preferred are R(+)-2-{2-[(5,6-dichloro-2,3,9,9a-tetrahydro-3-oxo-9a-propyl-1H-fluoren-7-yl)oxy]ethyl}-oxazoline, and the corresponding salts.

Also preferred is R(+)-2-[(5,6-dichloro-2,3,9,9a-tetrahydro-3-oxo-9a-propyl-1H-fluoren-7-yl)oxy] thiophene.

Also preferred is R(+)-7-(acetoxymethoxy)-5,6-dichloro-9a-propyl-2,3,9,9a-tetrahydro-1H-fluoren-3-one.

Also preferred are R-(+)-5,6-dichloro-9a-propyl-7-(3-pyridylmethoxy)-2,3,9,9a-tetrahydro-1H-fluoren-3-one, and the two isomeric compounds, R-(+)-5,6-dichloro-9a-propyl-7-(2-pyridylmethoxy)-2,3,9,9a-tetrahydro-1H-fluoren-3-one, and R-(+)-5,6-dichloro-9a-propyl-7-(4-pyridylmethoxy)-2,3,9,9a-tetrahydro-1H-fluoren-3-one, and the corresponding salts of each compound.

Also preferred is R(+)-7-acetoxy-5,6-dichloro-9a-propyl-2,3,9,9a-tetrahydro-1H-fluoren-3-one.

Also preferred are R(+)-5,6-dichloro-7-(2-dimethylaminoacetoxy)-9a-propyl-2,3,9,9a-tetrahydro-1H-fluoren-3-one, and the corresponding salts.

Also preferred is R(+)-N-[(2,2-dimethoxy)ethyl]-[(5,6-dichloro-2,3,9,9a-tetrahydro-3-oxo-9a-propyl-1H-fluoren-7-yl)oxy]acetamide.

Also preferred is R(+)-N-benzyl-[(5,6-dichloro-2,3,9,9a-tetrahydro-3-oxo-9a-propyl-1H-fluoren-7-yl)oxy] acetamide.

Also preferred is R(+)-N-(2-pyridylmethyl)-[(5,6-dichloro-2,3,9,9a-tetrahydro-3-oxo-9a-propyl-1H-fluoren-7-yl)oxy]acetamide, and the corresponding salts.

Also preferred is R(+)-N-[3-(1-imidazolyl)propyl][(5,6-dichloro-2,3,9,9a-tetrahydro-3-oxo-9a-propyl-1H-fluoren-7-yl)oxy]acetate, and the corresponding esters and salts.

Also preferred is R(+)-N-methyl-N-[(2-oxazolinyl) methyl]-[5,6-dichloro-2,3,9,9a-tetrahydro-3-oxo-9a-propyl-1H-fluoren-7-yl)oxy]acetamide, and the corresponding salts.

Especially preferred are the pure enantiomers since, in most instances, one enantiomer is more active biologically than its enantiomer.

Included within the scope of the preferred embodiments of this invention are the pharmaceutically acceptable salts of the novel compounds of this invention since a major medical use of these compounds is solutions of their soluble salts which can be administered parenterally.

Synthetic Methods for Preparing Compounds of the Invention

FIG. 1 depicts a "Method A" synthetic pathway used to prepare a fluorenone analog with improved biological activity. This synthesis, described in detail in Example 1, was used to prepare a compound designated as GERI-E1.

The "Method A" synthesis pathway disclosed in Example 1 and FIG. 1 can be modified in ways that will be obvious to those skilled in the art, to create a variety of other fluorenone analogs having 7-substituent groups that are bonded to the fluorene structure via ether linkages.

Figure 2:
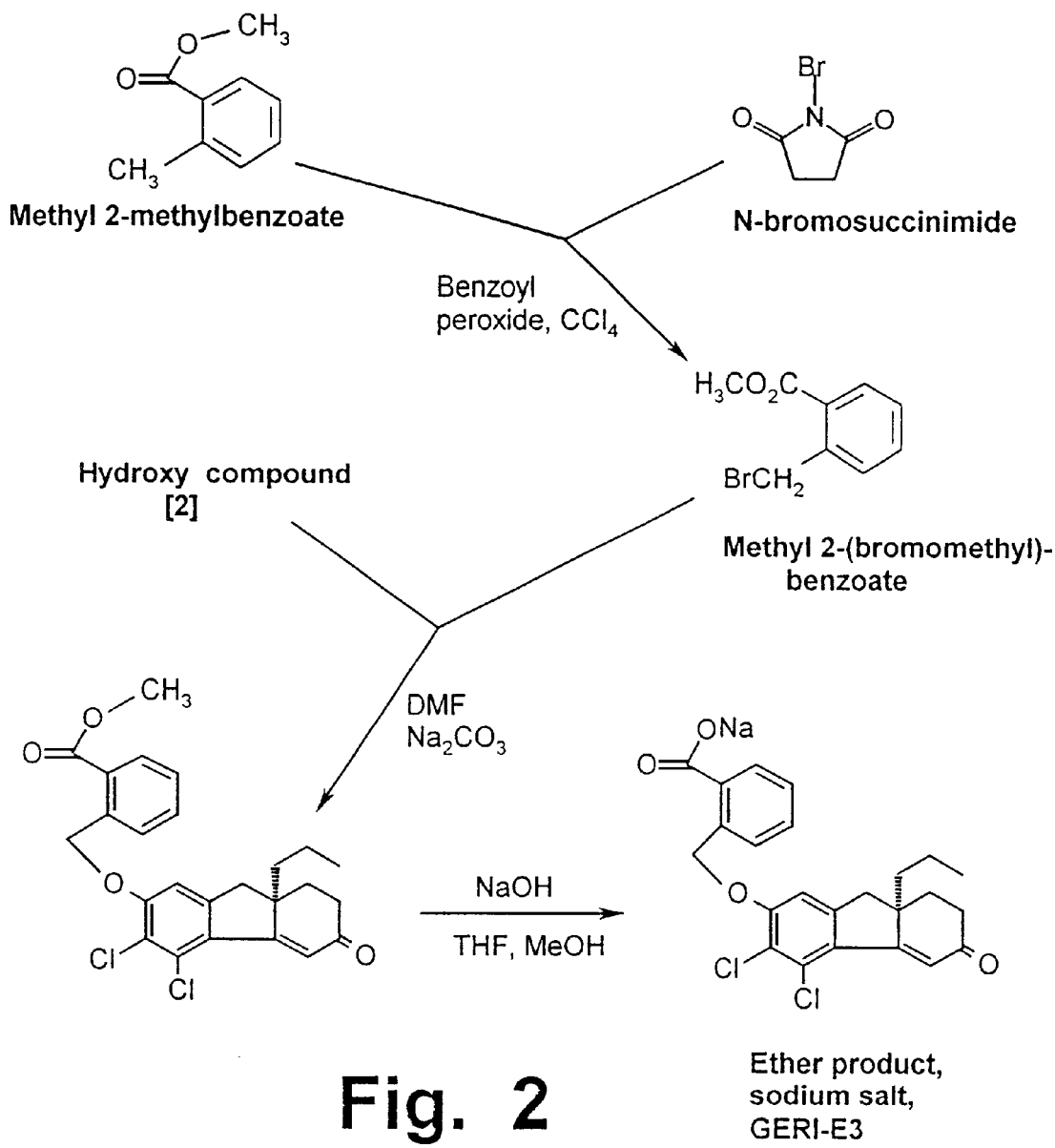
FIG. 2 depicts a "Method B" synthetic pathway used to prepare several other fluorenone ether analogs with improved biological activity. The syntheses of ortho, meta, and para isomers designated as GERI-E3, E4, and E5, are described in Examples 3, 4, and 5.

FIG. 2 depicts a "Method B" synthetic pathway used to prepare another fluorenone analog with improved biological activity, which can be viewed as an analog of L-644,711 bearing an ortho-interphenylene moiety inserted between the carboxy and methylene groups. This synthesis, described in detail in Example 3, was used to prepare a compound designated as GERI-E3.

In an analogous manner, similar processes were used to prepare the isomeric meta-interphenylene compound GERI-E4 (Example 4) and the isomeric para-interphenylene compound GERI-E5 (Example 5).

Figure 3:
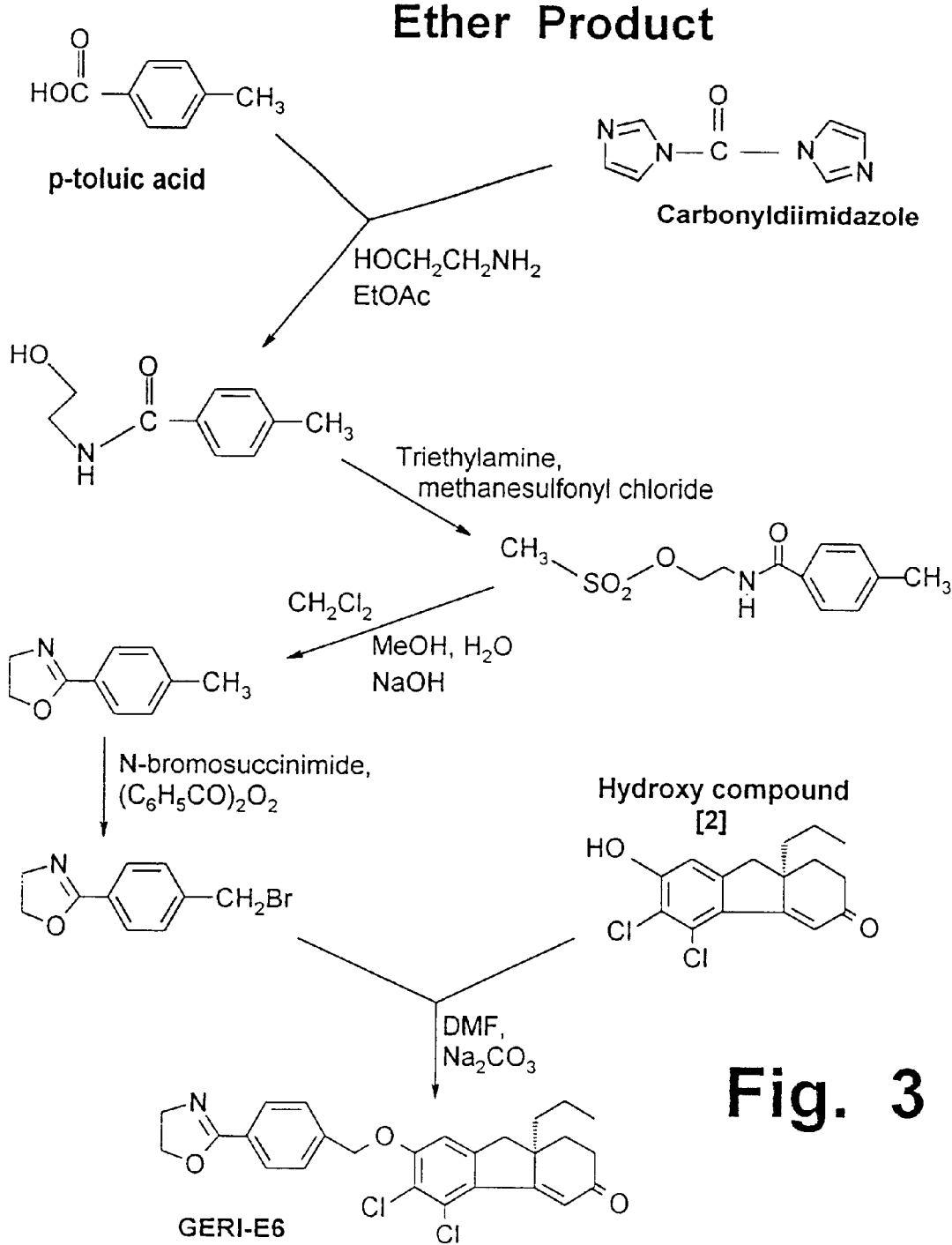
FIG. 3 depicts a "Method C" synthetic pathway used to create GERI-E6, a fluorenone ether analog containing a basic heterocyclic (2-oxazolinyl) group in place of the acidic carboxy group of compound GERI-E5. Similar pathways for creating other intermediates with heterocyclic rings and their reactions with hydroxy compound [2] are described in Examples 8 through 11.

FIG. 3 depicts a "Method C" synthetic pathway for preparing another fluorenone analog with improved biological activity, which can be viewed as an analog of GERI-E5 bearing a basic heterocyclic (2-oxazolinyl) group in place of an acidic carboxy group. This synthesis is described in detail in Example 6.

Figure 4:
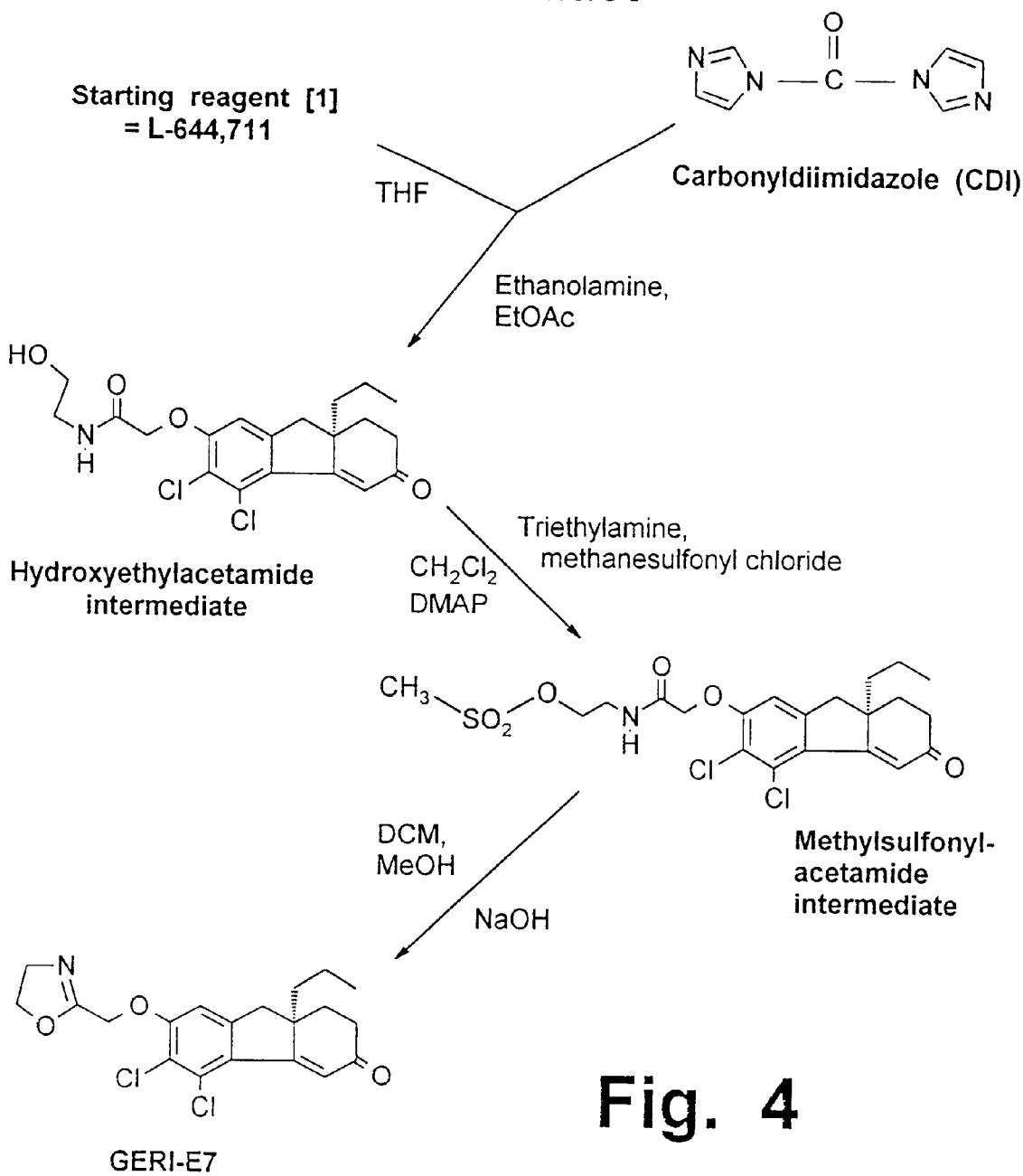
FIG. 4 depicts a "Method D" synthetic pathway used to create a basic heterocyclic 7-substituent. This 3-step synthetic pathway is described in detail in Example 7, and the resulting compound was designated as GERI-E7.

It should be noted that Methods A, B, and C all use brominated intermediates to form the desired ethers, as shown in FIGS. 1 through 3. By comparison, FIG. 4 depicts a completely different ("Method D") synthetic pathway to create various 7-heterocyclic-alkyl ethers by cyclization of the appropriate acyclic intermediate. An example of this synthesis pathway is described in Example 7, and was used to create compound GERI-E7. Because of its performance in the aspartate release assay, the GERI-E7 analog was selected for testing in animals. It was shown to be very effective in reducing brain damage caused by either global or focal brain ischemia in the animal models used.

Examples of intermediates for various other ether analogs with heterocyclic substituents at the 7-position, which can be prepared using variations of the "Method D" steps described in Example 7, are disclosed in Examples 8 through 11.

Figure 5:
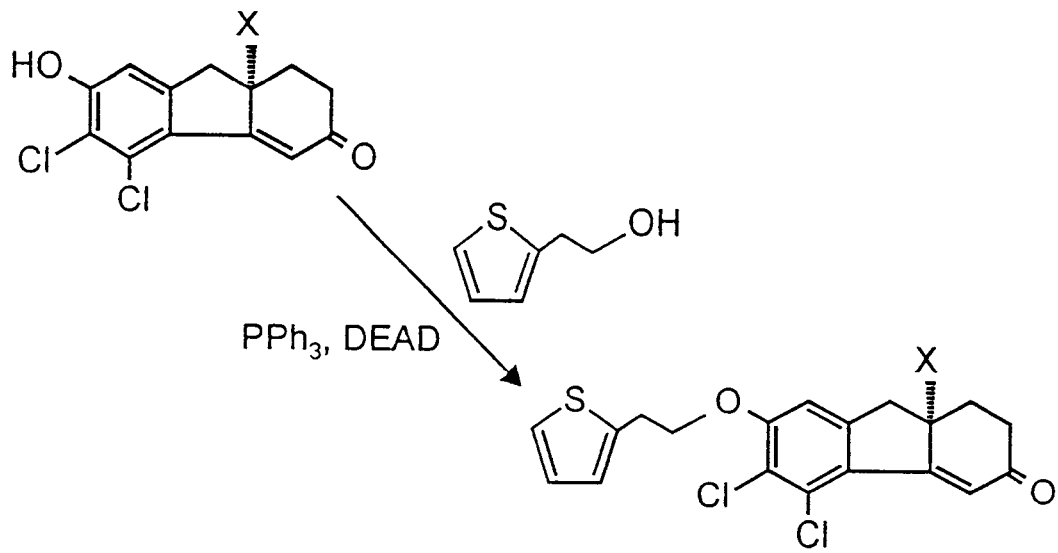
FIG. 5 depicts a "Method E" synthetic pathway which used an alcohol rather than brominated intermediate to create a fluorenone ether analog, designated as GERI-E12. This synthetic pathway is described in Example 12.

FIG. 5 shows yet another synthesis pathway, designated as "Method E", in which an alcohol intermediate reacts with compound [2]. This pathway was used to create analog GERI-12, as described in Example 12.

It should be noted that FIG. 5 also cites Cragoe et al, *J. Med. Chem* 29: 825–841 and U.S. Pat. Nos. 4,356,313 (Cragoe et al 1982) and 4,731,471 (Cragoe et al 1988). This prior art teaches how to introduce a selected group (such as a methyl, ethyl, propyl, or other alkyl group, a hydroxyethyl or other hydroxyalkyl group, and the like) to the 9a-position of a fluorenone structure, as indicated by the variable "X" group shown in FIG. 5. The pathway described in the cited article and patents uses an indanone reagent as a starting compound, and generates a fluorenone compound with the general structure as shown. Racemic forms can be resolved by procedures like those described in the cited article and patents.

Figure 6:
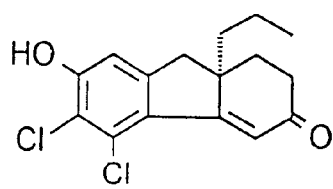
FIG. 6 depicts a general "Method A" for creating fluorenone analogs with substituents attached to the 7-position via ester linkages. This process was used to create an ester compound designated as GERI-Est1, described in Example 15. An alternate process for creating ester analogs is also shown as "Method B", which was used in Example 16 to give GERI-Est2.
Figure 6:
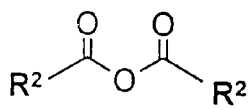
Figure 6:
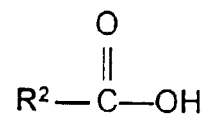
Figure 6:
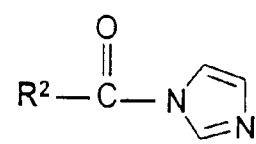
Figure 6:
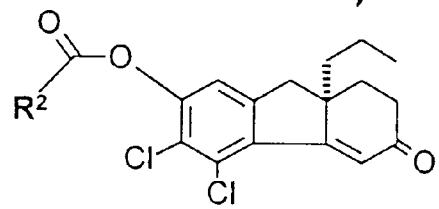

FIG. 6 illustrates a general "Ester Method A" for preparing esters derived from hydroxy compound [2]. This method, described in detail in Example 15, was used to generate R-(+)-7-acetoxy-5,6-dichloro-9a-propyl-2,3,9,9a-tetrahydro-1H-fluoren-3-one, designated as GERI-Est1. As suggested by FIG. 6, esters with other "$R^2$" groups at the 7-position can be generated, by using a different anhydride reagent having the desired $R^2$ groups. Since anhydrides tend to be difficult to prepare and work with, preferred $R^2$ groups for this approach include alkyl, substituted alkyl, aryl, and substituted aryl groups.

An alternate "Ester Method B" for creating ester linkages at the 7-position is described in Example 16. In this procedure, a reactant bearing a carboxylic acid group (such as N,N-dimethylglycine) is treated with carbonyldimidazole (CDI, shown in FIGS. 3 and 4). The hydroxy group from the carboxylic acid is replaced by a 1-imidazolyl group to generate a potent acylating compound. When this reacts with hydroxy compound [2], the desired ester linkage and a 7-substituent as shown for GERI-Est2 (shown in FIG. 9) is formed.

The use of N,N-dimethylglycine to generate compound GERI-Est2, using "Ester Method B", is described in Example 16. Variants of this procedure, using other reagents having carboxylic acid groups, can be used to generate fluorenones having other 7-substituents.

Figure 7:
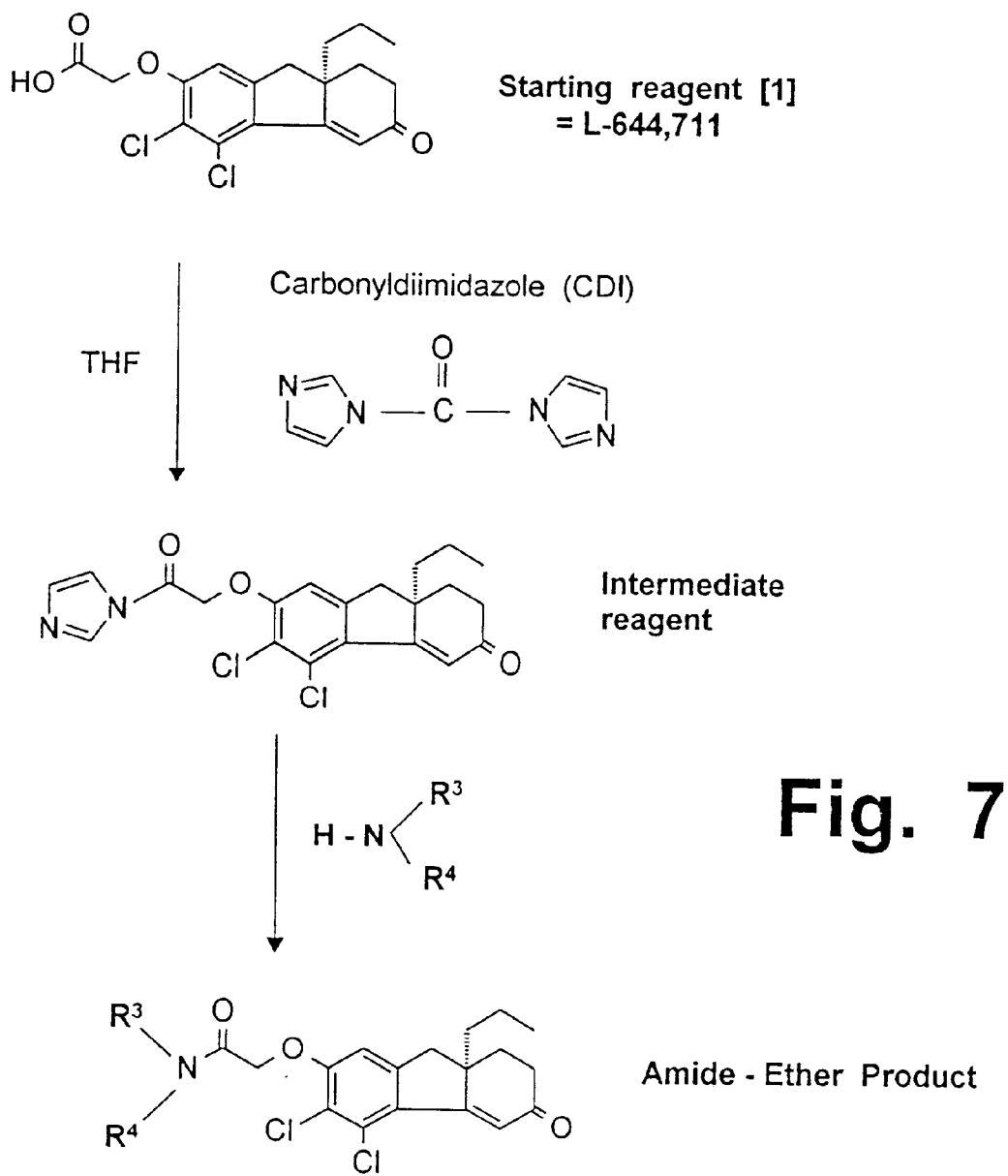
FIG. 7 depicts a method for creating fluorenone analogs with substituted aminocarbonylmethoxy substituents attached to the 7-position. These amide-ether compounds are designated as "GERI-AmE" compounds, as disclosed in Examples 17–22.

FIG. 7 illustrates a general method for synthesizing fluorenone analogs bearing a $R^3R^4NCOCH_2O-$ moiety in the 7-position. These compounds are referred to herein as "amide-ether" compounds, and are designated as the "GERI-AmE" series of compounds. Examples 17 through 22 describe the use of this method for generating a number of amide-ether compounds having the 7-substituents shown in FIG. 10.

Biological Tests; Structure-Activity Relationships

A number of the fluorenone analogs described in Examples 1–22 were tested for the ability to inhibit excitotoxin release by stressed astrocyte cells, using the assay procedures that are briefly described in Example 23.

Several exemplary results from these tests, expressed as $IC_{50}$ values, are provided in Table 1. These "inhibitory concentration, 50%" values indicate the micromolar concentration of a tested compound which was effective in suppressing the amount of aspartate released by the stressed astrocyte cells by 50%, when compared to stressed cell populations that were not treated by a test compound. A low $IC_{50}$ value indicates that a compound is highly potent.

TABLE 1

POTENCIES OF NEW COMPOUNDS IN SUPPRESSING
EXCITOTOXIN RELEASE BY STRESSED ASTROCYTE CELLS

| Compound | $IC_{50}$ value, $\mu M$ | Comparative potency |
| --- | --- | --- |
| L-644,711 (prior art) | 263.5 | 100% = benchmark |
| GERI-E1 | 29.5 | 893% |
| GERI-E3 | 7.9 | 3,335% |
| GERI-E4 | 7.8 | 3,378% |
| GERI-E5 | 8.0 | 3,294% |
| GERI-E7 | 8.5 | 3,100% |
| GERI-E13 | 19.2 | 1,372% |
| GERI-Est1 | 13.9 | 1,896% |
| GERI-AmE1 | 19.4 | 1,358% |
| GERI-AmE3 | 31.9 | 826% |
| GERI-AmE4 | 11.6 | 2,272% |
| GERI-AmE5 | 39.8 | 662% |

It is clear from the data in Table 1 that the newly developed GERI analogs are far more potent than the prior art L-644,711 compound, at inhibiting the release of aspartate by stressed glial cells. Indeed, these newly discovered potencies are dramatically and surprisingly strong compared to the benchmark compound, which was selected by Merck and Company in the late 1980's as the most promising fluorenone compound for additional research in animals. The most potent analog identified to date, GERI-E4, is nearly 34-fold (3,378%) more active than L-644,711; even the least active analog listed above, GERI-AmE5, is nearly 7-fold (662%) more potent than L-644,711.

Structure-activity studies indicate that at least six distinct types of structural modifications have produced dramatic and unexpected increases in biological activity for these fluorenone compounds, compared to the L-644,711 benchmark compound from the prior art:

1. Replacement of carboxy by a tri(hydroxymethyl) methyl group (e.g., GERI-E1);
2. Insertion of an ortho-, meta-, or para-interphenylene group between the methylene and carboxy group (e.g., GERI-E3, E4, and E5);
3. Replacement of carboxy by a 2-oxazolinyl group or similar heterocyclic groups (e.g., GERI-E7;
4. Replacement of carboxy by an acetoxy group (e.g., GERI-E13);
5. Replacement of carboxymethyl by an acetyl group (e.g., GERI-Est1);
6. Replacement of the hydroxy portion of carboxy by substituted-amino (e.g., GERI-AmE1, AmE3, AmE4, and AmE5).

Figure 11:
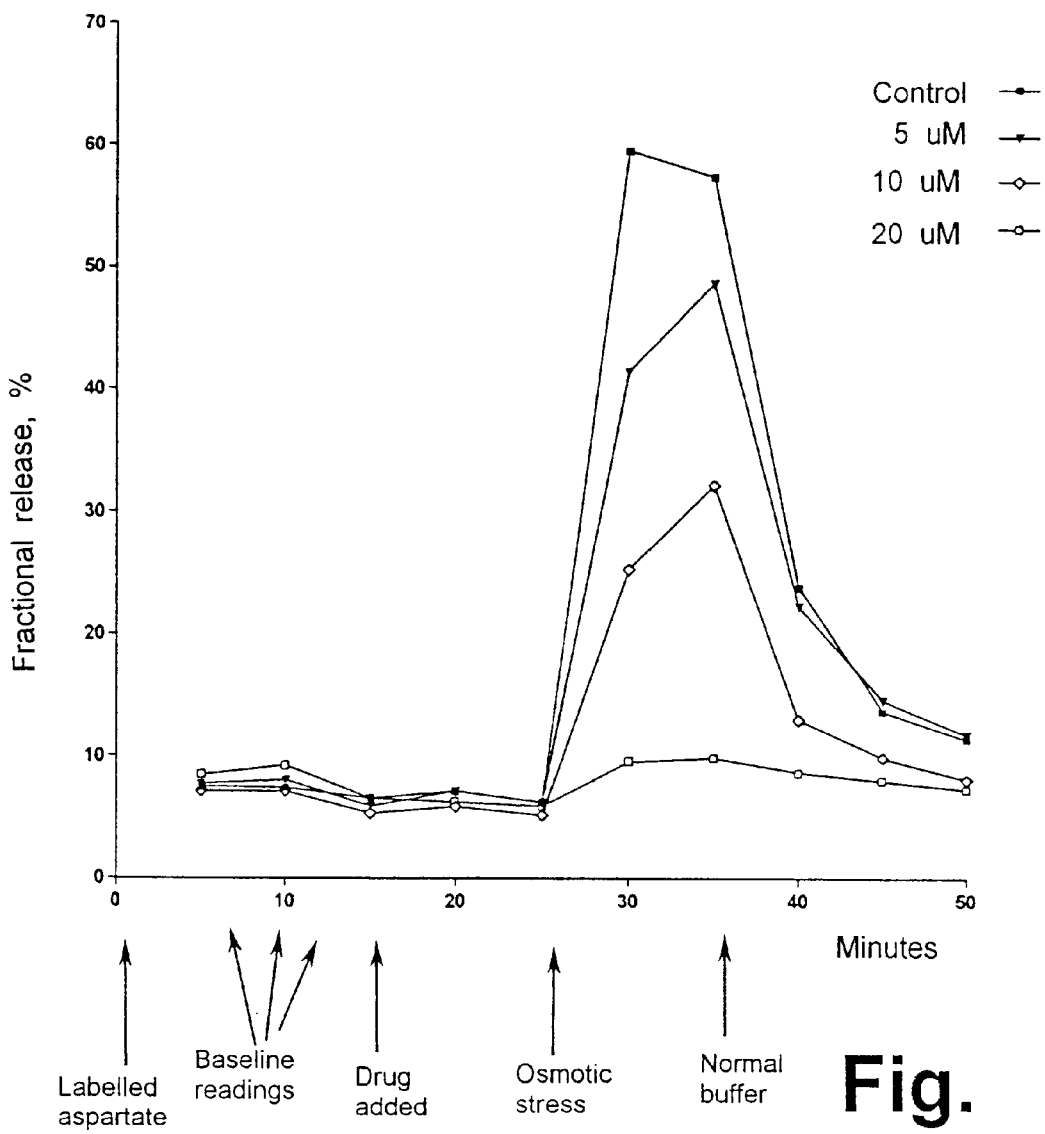
FIG. 11 depicts the results of excitotoxin release assays, described in Example 23, using the fluorenone analog designated as GERI-E7.

FIG. 11 displays the results obtained from essentially the same type of astrocyte cell test as discussed in connection with Table 1. The results are expressed as both a function of time and as a function of concentration. These results were obtained using three different concentrations of compound GERI-E7, which was selected as a lead compound for testing against global or focal brain ischemia.

The surgical and drug treatment procedures used in the animal model of global brain ischemia are described in Example 24. "Global" ischemia occurs when the entire brain is deprived of oxygenated blood, as occurs during crises such as cardiac arrest, suffocation, or carbon monoxide poisoning. It should be noted that the drug treatment was provided only after the ischemic insult had been fully completed (i.e., after the clamps which were used to temporarily close the carotid arteries had been released again). "Post-trauma" treatment offers a much more realistic, and much more difficult and stringent, challenge than other assays in which test animals are pre-treated with a test drug before an ischemic insult begins.

Figure 12:
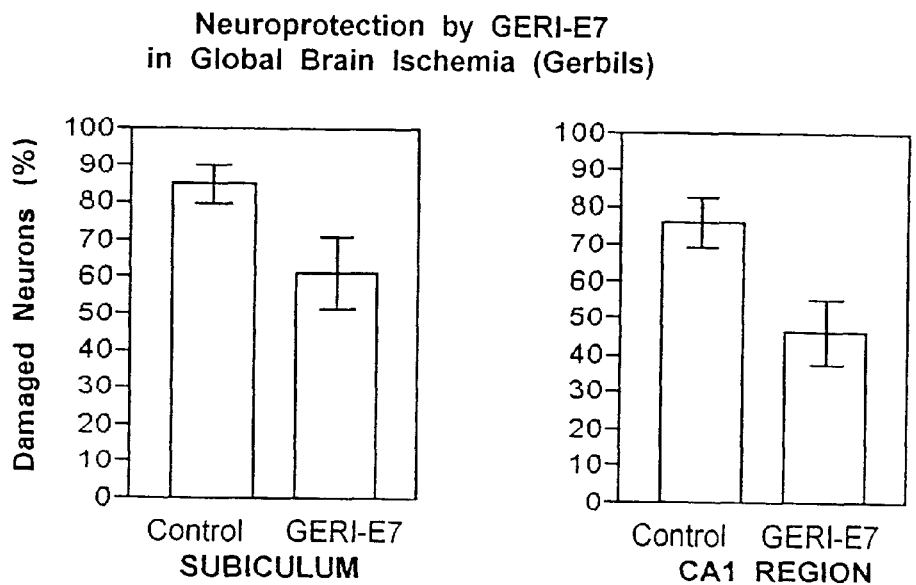
FIG. 12 depicts the results of in vivo assays which tested the ability of compound GERI-E7 to protect against brain damage caused by global brain ischemia in gerbils.

The results, graphically displayed in FIG. 12, clearly indicate that the GERI-E7 compound substantially reduced the number of dead or dying neurons in both of the brain regions that were analyzed (the subiculum, and the CA1 region of the hippocampus). In the subiculum, dead or dying neurons were reduced by about 30% on average. In the hippocampus, dead or dying neurons were reduced by about 40% on average. Since both of these two brain regions were chosen for analysis because they are extremely sensitive to ischemic damage, the GERI-E7 compound may well offer even greater levels of protection in most of the other regions of the brain.

Other in vivo tests were also carried out using "focal" brain ischemia (i.e., blood supply to only a portion of the brain is disrupted, as usually occurs during a stroke). These assays used a surgical procedure described in Example 25, in which the right middle cerebral artery (MCA) and the right common carotid artery (CCA) of rats were clamped shut for two hours. The clamps were then removed, and the GERI-E7 was administered subsequently. The rats were sacrificed 3 days later, and brain sections were analyzed using tetrazolium dye, to determine the volumes of brain tissue with large numbers of dead or dying neurons.

Figure 13:
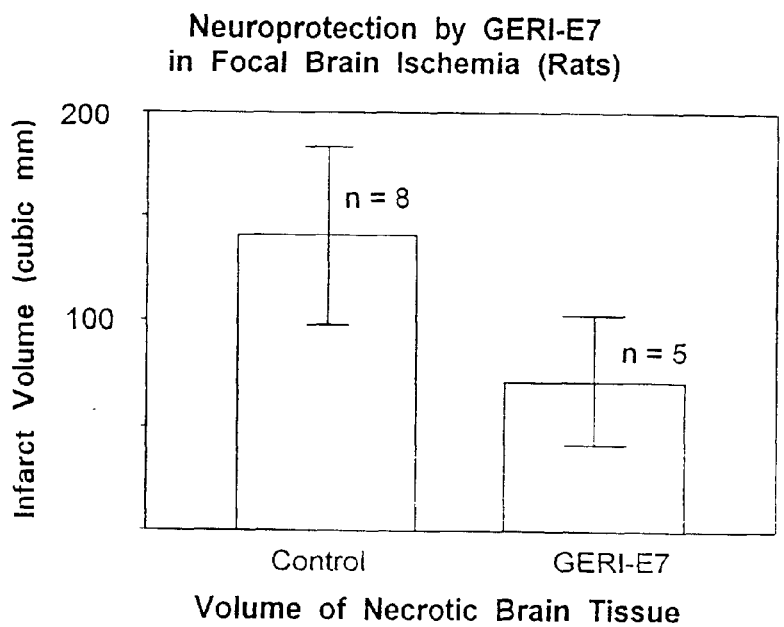
FIG. 13 depicts the results of in vivo assays which tested the ability of compound GERI-E7 to protect against brain damage caused by focal brain ischemia in rats.

The results from the first round of focal assays indicated that the GERI-E7 analog reduced "infarct volumes" by about 30%. A second set of assays, carried out using a new batch of GERI-E7 stored in liquid nitrogen and mixed with the carrier liquid less than 24 hours before injection, indicated that GERI-E7 reduced infarct volumes by an average of 50%. The results of these assays are shown in FIG. 13.

Mode of Administration, and Dosages

The compounds of this invention can be administered by any technique capable of introducing the compounds into the bloodstream, such as by intravenous, intramuscular, subcutaneous, intraperitoneal, or intracisternal injection, or by oral or rectal administration, or by any other suitable form of administration (such as transdermal, nasal, and the like), so long as any such route of administration provides adequate concentrations of the selected compound in the bloodstream.

If parenteral injection is used, the active compound must be administered in a suitable pharmaceutical formulation, such as an aqueous carrier vehicle. The nature of the carrier vehicle is not crucial to this invention, so long as it does not interfere with the desired pharmacological activity of the active agent. Such formulations may comprise a mixture of one or more active agents, mixed with one or more pharmaceutically acceptable carriers or diluents. Such formulations may also contain one or more compounds to increase the solubility of the active agent in the carrier vehicle, or to increase the extent to which the active agent will permeate through a mammalian blood-brain barrier and contact glial cells within the central nervous system.

Since the drugs of this invention are intended to be used to prevent or reduce brain damage in acute-care crises (such as immediately after a stroke, cardiac arrest, near-suffocation or asphyxiation, or severe blood loss, or in various other medical crises as listed in the Background section), the preferred mode of administration is intravenous injection or infusion.

If intravenous injection or infusion is used, preferred dosage ranges for the compounds disclosed herein will depend on factors which include the nature and severity of the medical crisis, the excitotoxin-release-inhibiting potency of the particular compound being used, and the ability of that compound to readily permeate the blood-brain barrier. In general, if injected intravenously in an initial bolus or within roughly 15 minutes of initial infusion, dosages in the range of about 0.05 to about 50 mg/kg (i.e., milligrams of drug per kilogram of patient body weight) are likely to be useful. These compounds are not for over-the-counter sale or use; instead, the preferred dosage for any specific patient will be determined by a physician or other health-care provider (such as an ambulance attendant) who administers the medication.

Dosages that are suited for prolonged infusions will depend on various factors such as the nature of the crisis, whether the patient is conscious and/or on a respirator or ventilator, how the patient's condition has responded to initial treatment efforts, and the time-dependent progression of the patient's neurological status. Accordingly, infusion dosages for prolonged administration must be determined for a specific patient by a treating physician.

Several of the compounds disclosed herein are prone to gradual chemical degradation due to hydrolysis, after they have been mixed with an aqueous carrier solution. Such hydrolysis is generally believed to accumulate gradually, over a span of several days or weeks, in those compounds in which hydrolysis has been observed. To avoid or minimize that problem, if a selected compound with otherwise desirable activities suffers from an undesirably high rate of hydrolysis, it can be manufactured using non-aqueous solvents (or, if necessary, the final preparative steps can be carried out using non-aqueous solvents or by taking steps to minimize the duration of any aqueous steps). Such compounds can be packaged in dehydrated form (with a desiccating agent if desired), and mixed with an aqueous carrier liquid (if such a carrier liquid is necessary) shortly before injection or other administration. Manufacturing methods, packaging devices, and reconstitution procedures that are suited for such handling are well-known and conventional in the art.

Salts and Enantiomers

The claims below refer to certain compounds as specifically listed, and to "enantiomers and pharmaceutically acceptable salts" of those compounds.

The term "pharmaceutically acceptable" as used herein embraces those characteristics which make a drug suitable and practical for administration to humans. For example, such a compound must be sufficiently chemically stable under reasonable storage conditions to have an adequate shelf life, and it must be physiologically acceptable and have an adequately low level of toxicity and adverse side effects, when introduced into the body by a suitable route of administration. If a compound is intended to be administered by injection, it preferably should have adequate solubility in water to allow it to be dissolved in an injectable aqueous carrier; however, solubilizing agents such as polyhydroxy compounds or dimethyl sulfoxide can be used to increase aqueous solubility, if necessary.

The term "therapeutically effective" as used herein means that an enantiomer or salt must be effective in reducing neuronal damage in at least one type of scientifically accepted in vivo model of ischemic, hypoxic, or other insult to the brain or spinal cord. Although such in vivo neuroprotective efficacy does not depend upon any sole or specific cellular mode of action, the neuroprotective activity and potency of such compounds is likely to correlate with either or both of the following, which can be measured by in vitro assays: (i) suppression of swelling of at least one type of glial cell (such as astrocyte cells), when such cells are subjected to appropriate types of osmotic, hypoxic, or ischemic stress; and, (ii) suppression of glutamate and/or aspartate release by glial cells that are subjected to appropriate types of osmotic, hypoxic, or ischemic stress.

The term "salts" can include salts of free acids or free bases. Examples of salts made from fluorenone analogs that are acidic (due to the 7-R group) include sodium, potassium, ammonium, trimethylammonium, piperazinium, guanidinium, 1-methylpiperazinium, bis-(2-hydroxyethyl) ammonium, N-methylglucosammonium salts, and the like.

Additionally, since some of the compounds of the invention are basic due to particular R constituents as set forth above, the invention as it relates to such basic compounds includes pharmaceutically acceptable salts such as the hydrochloride, hydrobromide, isothionate, maleate, sulfate, methanesulfonate, sulfate, acetate, succinate, and citrate salts and the like.

EXAMPLES

In the Examples below, any references to compound or reagent [1] refer to the prior art benchmark compound, L-644,711, which was used as a starting reagent in a number of the syntheses listed below. Compound [1], which is illustrated in FIG. 1, was prepared by the method described in Cragoe et al, *J. Med. Chem.* 29: 825–841 (1986).

Compound [2], also shown in FIG. 1, is the hydroxy (or phenol) intermediate that was used to prepare various ether and ester analogs. It was prepared by cleaving the carboxymethyl group from compound [1], as described in Cragoe et al, *J. Med. Chem.* 29: 825–841 (1986).

Figure 8A:
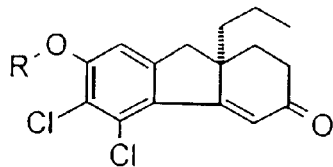
FIGS. 8A and 8B show the 7-substituents for various ether analogs designated as GERI-E1 through E14, described in Examples 1 through 14.
Figure 8B:
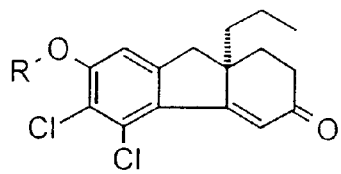
Figure 9:
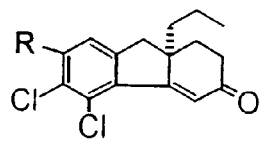
FIG. 9 shows the 7-(substituted acyloxy) analogs designated as GERI-Est1 and Est2, described in Examples 15 and 16.
Figure 10:
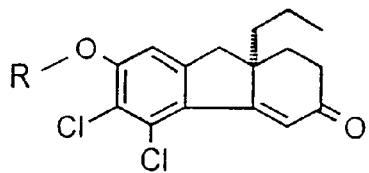
FIG. 10 shows the 7-(substituted aminocarbonylmethoxy) analogs designated as GERI-AmE1 through AmE6, described in Examples 17 through 22.

The final products described in Examples 1–22 have 7-substituents as shown in FIGS. 8A and 8B (ether compounds), FIG. 9 (ester compounds), and FIG. 10 (amide-ether compounds).

Example 1

Synthesis of GERI-E1=R-(+)-5,6-dichloro-7-[3-hydroxy-2,2-bis-(hydroxymethyl)propyloxy]-9a-propyl-2,3,9,9a-tetrahydro-1H-fluoren-3-one Synthesis of this compound required a brominated reagent that was prepared by dissolving 2-(bromomethyl)-2-(hydroxymethyl)-1,3-propanediol (288 mg, 1.44 mmol) and 3,4-dihydro-2H-pyran (2.16 g, 25.7 mmol) in dry methylene chloride. A catalytic amount of p-toluenesulfonic acid (52 mg) was added and the reaction was stirred at room temperature. Thin layer chromatography (TLC; 10% EtOAc/hexane) indicated complete reaction after 2 hrs. The reaction mixture was diluted with methylene chloride and washed with water. Silica gel chromatography (10% EtOAc/hexane) furnished 0.60 g (93%) of 2-(bromoethyl)-2-(tetrahydropyran-2-yloxymethyl)-1,3-bis(tetrahydropyran-2-yloxy)propane, which is illustrated in FIG. 1. MS m/z 468/470 $(M+NH_4)^+$, 473/475 $(M+Na)^+$.

This bromoethyl intermediate (0.73 g, 1.6 mmol) was added to a mixture of compound [2] (390 mg, 1.26 mmol) that had been dissolved in dry DMF (3 ml) and sodium carbonate (1.1 g). The mixture was heated to 80° C. When TLC (10% MeOH/CHCl$_3$) indicated the reaction was complete, the mixture was diluted with EtOAc and washed with water. The organic phase was dried with sodium sulfate, filtered, evaporated, and chromatographed on silica gel (10% MeOH/CHCl$_3$) to give 0.72 g (84% yield) of the second intermediate, also illustrated in FIG. 1 (MS m/z 703/705 $(M+Na)^+$).

This second intermediate (675 mg, 0.99 mmol) was dissolved in MeOH (15 ml), then water (5 ml) and TFA (5 ml) were added. The reaction was stirred at room temperature until TLC (20% MeOH/CHCl$_3$) indicated a complete reaction. The mixture was evaporated to dryness and the product was isolated by silica gel chromatography (20% MeOH/CHCl$_3$). A total of 205 mg (48%) of the final product was obtained. $^1$H-NMR (500 Mhz, CDCl$_3$): Σ=6.88 (s, 1H), 6.80 (s, 1H), 4.17 (s, 2H), 3.85 (s, 6H), 2.99 (d, 1H), 2.72 (d, 1H), 2.56 (ddd, 1H), 2.45 (dd, 1H), 2.26 (dd, 1H), 1.97 (ddd, 1H), 1.59 (ddd, 1H), 1.46 (ddd, 1H), 1.27 (m, 1H), 1.16 (m, 1H), 0.86 (t, 3H). MS m/z 467 $(M+K)_+$, 463/465 (M+Cl).

Example 2

Synthesis of GERI-E2=R(+)-7-(2-aminoethyl)-5,6-dichloro-2,3,9,9a-tetrahydro-9a-propyl-1H-fluoren-2-one This compound is prepared as in Example 1, except that the methyl 3-(bromomethyl)benzoate is replaced by an equimolar amount of N-(2-bromoethyl)phthalimide. Hydrolysis of the first formed 7-[(2-phthalimido)ethoxy] compound provides the desired product, designated as GERI-E2.

Example 3

Synthesis of GERI-E3=Sodium R(+)-2-[(5,6-dichloro-2 3,9,9a-tetrahydro-3-oxo-9a-propyl-1H-fluoren-7-yl)oxymethyl]benzoate To prepare a methyl 2-(bromomethyl)benzoate reagent, methyl 2-methylbenzoate (Aldrich Chemical Co., 5.97 g, 40.0 mmol) was treated with N-bromosuccinimide (7.1 g, 40.0 mmol) in the presence of benzoyl peroxide (53 mg) in tetrachloromethane. The reaction mixture was refluxed overnight under N$_2$ atmosphere, and was monitored by TLC using 5% EtOAc/hexane. After the reaction was completed, the solvent was removed by evaporation and the residue was separated between water and EtOAc. The organic phase was washed with water, dried with sodium sulfate, filtered and evaporated to give a colorless oil containing methyl 2-(bromomethyl)benzoate (9.0 g, quantitative yield), which was used without purification in the next step.

Compound [2] (1.1 g, 3.5 mmol) was dissolved in dry DMF (5 ml) and sodium carbonate (1.5 g) was added. The methyl 2-(bromomethyl)benzoate compound described above (1.1 g, 4.8 mmol) was added, and the mixture was heated to 50° C. When TLC (100% toluene) indicated complete reaction, the mixture was poured on ice. The precipitate was separated by filtration and chromatographed on silica gel (hexane/toluene/EtOAc 5:5:1) to give 1.24 g of the methyl ester intermediate (78% yield).

To hydrolyze the methyl ester and convert the intermediate carboxylic acid into the sodium salt, the intermediate (1.2 g, 2.6 mmol) was dissolved in THF/methanol (100 ml, 1:1). NaOH pellets (2 g) were added, and the reaction was stirred at room temperature. When TLC (100% EtOAc) indicated complete reaction, the mixture was evaporated to dryness. The crude residue was purified by silica gel chromatography using 60% EtOAc/toluene, then 100% EtOAc, and finally 100% THF. 360 mg (30%) of the sodium salt product were obtained. $^1$H-NMR (500 Mhz, DMSO-d$_6$): δ=7.93 (d, 1H), 7.56 (d, 1H), 7.39 (t, 1H), 7.26 (bs, 1H), 7.11 (s, 1H), 6.52 (s, 1H), 5.79 (d, 1H), 5.68 (d, 1H), 2.48 (d, 1H), 2.24 (d, 1H), 2.02 (m, 1H), 1.82 (m, 1H), 1.45 (m, 1H), 1.26 (m, 1H), 1.09 (m, 1H), 0.92 (m, 1H), 0.70 (t, 3H). MS m/z 445/447 $(M+H)^+$, 443/445 $(M-H)^-$.

Example 4

Synthesis of GERI-E4=Sodium R(+)-3-[(5,6-dichloro-2,3 9,9a-tetrahydro-3-oxo-9a-propyl-1H-fluoren-7-yl)oxymethyl]benzoate Compound [2] (820 mg, 2.63 mmol) was dissolved in dry DMF (5 ml). Sodium carbonate (1.5 g) was added. Methyl 3-(bromomethyl)benzoate (600 mg, 2.63 mmol), which is commercially available from Lancaster Synthesis Inc. (Windham, N.H.) was added and the mixture was heated to 80° C. When TLC (EtOAc/hexane 1:1) indicated that the reaction was complete, the mixture was poured onto ice. The precipitate was separated by filtration and dried to give 810 mg of the methyl ester intermediate.

To convert this intermediate into the sodium salt, the intermediate (0.8 g, 1.74 mmol) was dissolved in THF/MeOH 1:1 (30 ml). 50% NaOH (2.6 ml) was added and the solution was stirred overnight at room temperature. After silica gel chromatography with 100% EtOAc, 130 mg (16%) of product were obtained. $^1$H-NMR (500 MHz, DMSO-d$_6$): δ=8.07 (s, 1H), 7.95 (d, 1H), 7.53 (d, 1H), 7.41 (t, 1H), 7.31 (s, 1H), 6.56 (s, 1H), 5.27 (s, 2H), 3.00 (d, 1H), 2.74 (d, 1H), 2.53 (m, 1H), 2.28 (m, 1H), 2.16 (m, 1H), 1.96 (m, 1H), 1.55 (m, 1H), 1.35 (m, 1H), 1.20 (m, 1H), 1.07 (m, 1H), 0.78 (t, 3H). MS m/z 445/447 $(M+H)^+$, 443/445 $(M-H)^-$.

Example 5

Synthesis of GERI-E5=Sodium R(+)-4-[(5,6-dichloro-2,3,9,9a-tetrahydro-3-oxo-9a-propyl-1H-fluoren-7-yl)oxymethyl]benzoate The methyl ester derivative was prepared by dissolving the hydroxy intermediate (compound [2]; 311 mg, 1.0 mmol) in dry DMF (2 ml), and adding potassium carbonate (0.5 g). Methyl 4-(bromomethyl)benzoate (sold by Aldrich Chemical Co.; 235 mg, 1.03 mmol) was added and the mixture was heated to 80° C. When TLC (EtOAc/hexane 1:1) indicated complete reaction, the mixture was poured on to ice. The precipitate was separated by filtration, and dried to give 416 mg of the methyl ester intermediate.

To hydrolyze the ester and generate a sodium salt, the methyl ester intermediate (200 mg, 0.43 mmol) was dissolved in THF/MeOH 1:1 (5 ml). 1 N NaOH (2 ml) was added and the solution was stirred overnight at room temperature. The solvent was evaporated, the residue was dissolved in water and the solution was acidified with 1 N hydrochloric acid. The product was extracted with chloroform. The combined organic phases were dried with magnesium sulfate and filtered. Dowex 50WX8-200 ion exchanger (Na$^+$-form) was added and the solution was stirred for 15 min. It was then filtered and evaporated. The product was purified by silica gel chromatography using THF/EtOAc (1:1) as an eluent. 126 mg (62%) of a yellow product was obtained.

$^1$H-NMR (500 MHz, DMSO-d$_6$) data for the sodium salt: δ=7.99 (d, 2H), 7.59 (d, 2H), 7.35 (s, 1H), 6.59 (s, 1H), 5.39 (s, 2H), 3.03 (d, 1H), 2.79 (d, 1H), 2.55 (m, 1H), 2.3 (m, 1H), 2.18 (m, 1H), 1.99 (m, 1H), 1.57 (m, 1H), 1.37 (m, 1H), 1.24 (m, 1H), 1.08 (m, 1H), 0.80 (t, 3H). MS m/z 446 (M+H)$^+$, 443/445 (M−H)$^−$.

Example 6

Synthesis of GERI-E6=R(+)-5,6-dichloro-2,3,9,9a-tetrahydro-7-[4-(2-oxazolinyl)phenylmethoxyl]-9a-propyl-1H-fluoren-3-one This synthesis requires a brominated intermediate, which is prepared by a four-step process, as illustrated in FIG. 3. p-Toluic acid is first converted to N-(2-hydroxyethyl)-4-toluamide, using carbonyldiimidazole (CDI) and ethanolamine. This first intermediate is then converted to a N-[2-methanesulfonyloxy]-4-toluamide, using methanesulfonyl chloride. This second intermediate is then cyclized to form 2-(4-methylphenyl)oxazoline by processes analogous to those described in Example 7, below. This third intermediate is then brominated, using N-bromosuccinimide and benzoyl peroxide as described in Example 3, to produce 2-[(4-bromomethyl)phenyl]-oxazoline. This intermediate is then reacted with hydroxy compound [2], using a procedure similar to that described in Example 3, to give the desired compound, GERI-E6.

For the preparation of the two isomers of GERI-E6, wherein the (2-oxazolinyl) group is attached to the phenyl group in the 2- or 3-position, respectively, o-toluic acid or m-toluic acid serves as the starting material. The remaining three synthetic steps are conducted in a manner analogous to that described for the synthesis of GERI-E6.

Example 7

Synthesis of GERI-E7=R(+)-2-[[(5,6-dichloro-2,3,9,9a-tetrahydro-3-oxo-9a-propyl-1H-fluoren-7-yl)-oxy]methyl] oxazoline This compound was synthesized in three major steps, as shown in FIG. 3. In the first step, compound [1] (365 mg, 1.0 mmol) was dissolved in dry THF (2 ml), and CDI (200 mg, 1.2 mmol) was added. The mixture was stirred for 5 min and ethanolamine (92 mg, 1.5 mmole) was added. After TLC (15% MeOH/CHCl$_3$) indicated complete reaction, EtOAc was added to the reaction mixture and washed with 10% aqueous citric acid solution and then water. The organic phase was dried with sodium sulfate, evaporated, and purified by silica gel chromatography (15% MeOH/CHCl$_3$). This produced 380 mg (93% yield) of R(+)-N-[2-hydroxyethyl][(5,6-dichloro-2,3,9,9a-tetrahydro-3-oxo-9a-propyl-1H-fluoren-7-yl)oxy]acetamide. $^1$H-NMR (500 MHz, CDCl$_3$): δ=7.21 (bs, 1H), 6.86 (s, 1H), 6.79 (s, 1H), 4.60 (s, 2H), 3.82 (t, 2H), 3.58 (q, 2H), 3.02 (d, 1H), 2.76 (d, 1H), 2.58 (ddd, 1H), 2.40 (dd, 1H), 2.29 (m, 1H), 2.02 (m, 1H), 1.62 (m, 2H), 1.47 (m, 2H), 0.87 (t, 3H). MS m/z 412/414 (M+H)$^+$, 410/412 (M−H)$^−$.

In the second major step, the above-described hydroxyethyl-acetamide intermediate (380 mg; 0.92 mmol) and 200 μl triethylamine were dissolved in 15 ml dichloromethane (DCM). Methanesulfonyl chloride (100 μl, 1.3 mmol) was added dropwise. After stirring overnight, more methanesulfonyl chloride (150 μl) and a catalytic amount of 4-(dimethylamino)pyridine (DMAP) were added. After TLC (15% MeOH/CHCl$_3$) indicated complete reaction, the mixture was diluted with EtOAc and washed with water. The organic phase was dried with sodium sulfate, filtered and evaporated. This second intermediate, R-(+)-N-[2-methylsulfonyloxy][(5,6-dichloro-2,3,9,9a-tetrahydro-3-oxo-9a-propyl-1H-fluoren-7-yl)oxy]-acetamide, was used without further purification.

In the third step, the above-described methylsulfonyl-acetamide intermediate was dissolved in a minimum amount of dichloromethane. MeOH (5 ml) and water (1 ml) were added. Hydrolysis was started by the addition of a sodium hydroxide pellet (0.2 g). The reaction was stirred for 30 minutes, then washed with water three times. The organic phase was washed with saturated sodium bicarbonate solution and finally with water. It was then dried with sodium sulfate, filtered and evaporated. $^1$H-NMR (500 MHz, CDCl$_3$): δ=6.89 (s, 1H), 6.86 (s, 1H), 4.85 (s, 2H), 3.38 (t, 2H), 3.96 (t, 2H), 3.00 (d, 1H), 2.75 (d, 1H), 2.57 (ddd, 1H), 2.47 (dd, 1H), 2.27 (m, 1H), 2.00 (m, 1H), 1.61 (ddd, 1H), 1.48 (ddd, 1H), 1.29 (m, 1H), 1.20 (m, 1H), 0.87 (t, 3H). MS m/z 394/396 (M+H)$^+$, 392/394 (M−H)$^−$.

This compound, designated as GERI-E7, was highly potent as measured by the D-aspartate release assay, and had an IC$_{50}$ value of 8.5 μM. Because of how it performed in various in vitro assays, this compound was chosen as the primary candidate for subsequent testing in the in vivo animal assays, described below in Examples 24 and 25.

Example 8

Synthesis of GERI-E8=R(+)-2-{[(5,6-dichloro-2,3,9,9a-tetrahydro-3-oxo-9a-(2-hydroxyethyl)-1H-fluoren-7-yl)oxy]methyl}-2-oxazoline The starting material for this synthesis is R(+)[(5,6-dichloro-2,3,9,9a-tetrahydro-9a-(2-hydroxyethyl)-3-oxo-1H-fluoren-7-yl)oxy]acetic acid, prepared as described in Cragoe et al, *J. Med. Chem.* 29: 825–841 (1986). This compound has the same structure as the L-644,711 benchmark compound, except that it has a 2-hydroxyethyl group in the 9a-position, rather than a propyl group.

An equimolar amount of this compound is used in place of compound [1] in the first step of Example 7 to give the corresponding N-(2-hydroxyethyl)amide. Treatment of this compound with twice the molar amount of methanesulfonyl chloride as described in Example 7 gives the product bearing a methanesulfonyl ester moiety on each hydroxyl oxygen atom. Using this ester as described in the last step of Example 7, except that double the molar amount of NaOH is used, produces the desired product, which is designated as GERI-E8.

Example 9

Synthesis of GERI-E9=R(+)-2-{[(5,6-dichloro-2,3,9,9a-tetrahydro-3-oxo-9a-propyl-1H-fluoren-7-yl)oxy]-methyl}thiazoline This compound is prepared in five steps, beginning with R(+)-N-[2-hydroxyethyl][(5,6-dichloro-2,3,9,9a-tetrahydro-3-oxo-9a-propyl-1H-fluoren-7-yl)oxy]acetamide, prepared as described in the first step of Example 7. In the first step, reaction of this compound with ethylene glycol and p-toluene-sulfonic acid gives the corresponding 3-spiroketal compound. In the second step, treatment of the spiroketal compound with Lawesson's reagent gives the corresponding thioamide. Reaction of the thioamide with methanesulfonyl chloride and triethylamine, in a process like the second step described in Example 7, gives the corresponding methanesulfonyl ester (step 3). Ring closure of this ester, using sodium hydroxide, gives the 3-spiroketal of the desired product (step 4). In the final step, treatment of the spiroketal intermediate with trifluoroacetic acid gives the product named above, designated as GERI-E9.

Example 10

Synthesis of GERI-E10=R(+)-2-{[(5,6-dichloro-2,3,9,9a-tetrahydro-3-oxo-9a-propyl-1H-fluoren-7-yl)oxy]-methyl}-tetrahydro-1,3-oxazine This compound is prepared by the 3-step process described in Example 7, except an equimolar amount of 3-aminopropanol is used in place of ethanolamine.

Example 11
Synthesis of GERI-E11=R(+)-5,6-dichloro-7-[2-(2-oxazolinyl)ethoxy]-2,3,9,9a-tetrahydro-9a-propyl-1H-fluoren-3-one This compound is prepared as described in Example 1 except that an equimolar amount of 2-(2-bromoethyl) oxazoline is used in place of 2-(2-bromoethyl)-2-(tetrahydropyran-2-yloxymethyl)-1,3-bis-(tetrahydropyran-2-yloxy)propane.

The required intermediate, 2-(2-bromoethyl)oxazoline, is prepared in a two-step process starting with 3-bromopropionic acid. Reaction of this acid with CDI followed by ethanolamine gives N-(2-hydroxyethyl)-3-bromopropionamide. Treatment of this compound with triphenylphosphine (PPh$_3$) and DEAD in THF yields 2-(2-bromoethyl)oxazoline.

Example 12
Compound GERI-E12: R(+)-2-[[(5,6-dichloro-2,3,9,9a-tetrahydro-3-oxo-9a-propyl-1H-fluoren-7-yl)oxy]-ethyl] thiophene Triphenylphosphine (TPP; 254 mg, 0.97 mmol) and diethyl azodicarboxylate (DEAD; 153 µl, 0.97 mmol) were dissolved in dry THF and stirred for 5 min. Hydroxy compound [2] (100 mg, 0.32 mmol) was added and after an additional 5 minutes, 2-(2-thienyl)ethanol (110 µl, 1.0 mmol) was added. When TLC (EtOAc/toluene 1:4) indicated the reaction was complete, the products were separated between EtOAc and water. The organic phase was dried with sodium sulfate, filtered, and evaporated. Silica gel chromatography using hexane/EtOAc 3:1 provided 200 mg (67% yield) of the product. $^1$H-NMR (500 MHz, CDCl$_3$): δ=7.18 (m, 1H), 6.97 (m, 2H), 6.85 (s, 1H), 6.77 (s, 1H), 4.27 (t, 2H), 3.40 (t, 2H), 3.96 (d, 1H), 2.72 (d, 1H), 2.57 (ddd, 1H), 2.46 (dd, 1H), 2.26 (m, 1H), 2.00 (ddd, 1H), 1.60 (ddd, 1H), 1.47 (ddd, 1H), 1.28 (m, 1H), 1.17 (m, 1H), 0.86 (t, 3H).

The synthesis of this compound, designated as GERI-E12, serves as an example of a synthetic route that uses an alcohol intermediate rather than a brominated intermediate to generate a final ether product.

Example 13
Synthesis of GERI-E13=R-(+)-7-(acetoxymethoxy)-5,6-dichloro-9a-propyl-2,3,9,9a-tetrahydro-1H-fluoren-3-one This compound was synthesized by dissolving hydroxy intermediate [2] (168 mg, 0.54 mmol) in dry DMF (3 ml). Sodium carbonate (170 mg) and bromomethyl acetate (248 mg, 1.6 mmol) were added and the mixture was stirred at room temperature. When TLC (10% EtOAc/toluene) indicated the reaction was complete, the mixture was diluted with methylene chloride and washed with water, 1N NaOH, and again with water. The organic phase was dried with sodium sulfate, filtered, evaporated, and chromatographed on silica gel (30% EtOAc/hexane) to give 164 mg (79% yield) of the product. $^1$H-NMR (500 MHz, CDCl$_3$): δ=7.01 (s, 1H), 6.88 (s, 1H), 5.84 (s, 2H), 3.03 (d, 1H), 2.77 (d, 1H), 2.58 (ddd, 1H), 2.48 (dd, 1H), 2.29 (dd, 1H), 2.02 (ddd, 1H), 1.62 (m, 1H), 1.49 (ddd, 1H), 1.30 (m, 1H), 1.19 (m, 1H), 0.88 (t, 3H). MS m/z 383/385 (M+H)$^+$, 405/407 (M+Na)$^+$.

Example 14
Synthesis of GERI-E14=R(+)-5,6-dichloro-9a-propyl-7-(3-pyridylmethoxy)-2,3,9,9a-tetrahydro-1H-fluoren-3-one This compound is prepared as described in the first step of Example 4, except that an equimolar amount of (3-bromomethyl)pyridine hydrobromide is used instead of methyl 3-(bromomethyl)benzoate, and the molar amount of sodium carbonate is doubled.

The 2-pyridylmethoxy (ortho) and 4-pyridylmethoxy (para) isomers can also be prepared by essentially the same method, by using either (2-bromomethyl)pyridine hydrobromide or (4-bromomethyl)pyridine hydrobromide as a starting reagent, in place of (3-bromomethyl)pyridine hydrobromide as described above.

Example 15
Synthesis of GERI-Est1=R-(+)-7-acetoxy-5,6-dichloro-9a-propyl-2,3,9,9a-tetrahydro-1H-fluoren-3-one Hydroxy compound [2] (220 mg, 0.7 mmol) was dissolved in dry pyridine (3 ml). 4-(Dimethylamino)pyridine (60 mg) was added, then acetic anhydride (3 ml) was added dropwise. The reaction was stirred at room temperature until TLC (EtOAc/hexane 1:1) indicated the reaction was complete. The mixture was diluted with EtOAc and washed with water, 10% citric acid solution, saturated sodium bicarbonate solution, and again with water. The organic phase was dried with sodium sulfate, filtered, and evaporated. Silica gel chromatography (30% EtOAc/hexane) furnished 200 mg (80% yield) of the product. $^1$H-NMR (500 MHz, CDCl$_3$): δ=7.06 (s, 1H), 6.92 (s, 1H), 3.03 (d, 1H), 2.77 (d, 1H), 2.58 (ddd, 1H), 2.48 (dd, 1H), 2.29 (dd, 1H), 2.01 (ddd, 1H), 1.61 (m, 1H), 1.49 (ddd, 1H), 1.30 (m, 1H), 1.22 (m, 1H), 0.88 (t, 3H). MS m/z 375/377 (M+Na)$^+$.

This synthetic pathway, which uses an anhydride reagent to create an ester product, is regarded as "Method A" for ester synthesis. It is illustrated, in general terms, on the left side of FIG. 6.

Example 16
Synthesis of GERI-Est2=R(+)-5,6-dichloro-7-[2-(dimethylamino)acetoxy]-9a-propyl-2,3,9,9a-tetrahydro-1H-fluoren-3-one This compound is prepared by first reacting N,N-dimethylglycine with CDI in THF, to generate 1-(dimethylaminoacetyl)-imidazole. This intermediate is then treated with compound [2] under conditions that generate the dimethylaminoacetoxy compound designated as GERI-Est2.

Example 17
Synthesis of GERI-AmE1=R(+)-N-[2,2-(dimethoxy)-ethyl][(5,6-dichloro-2,3,9,9a-tetrahydro-3-oxo-9a-propyl-1H-fluoren-7-yl)oxy]acetamide Compound [1] (370 mg, 1 mmol) was dissolved in dry THF (2 ml). CDI (200 mg, 1.2 mmol) and aminoacetaldehyde dimethylacetal (200 µl, 1.8 mmol) were added. When TLC (10% MeOH/CH$_2$Cl$_2$) indicated complete reaction, diethyl ether was added and the solution was washed with water. The organic phase was dried with magnesium sulfate, filtered, and evaporated to give 380 mg of the crude product. After recrystallization from MeOH/water 220 mg (47% yield) of pure product were obtained. $^1$H-NMR (500 MHz, CDCl$_3$): δ=6.95 (bt, 1H), 6.79 (s, 1H), 6.71 (s, 1H), 4.51 (s, 2H), 4.37 (t, 1H), 3.46 (t, 2H), 3.34 (s, 6H), 2.95 (d, 1H), 2.67 (d, 1H), 2.51 (m, 1H), 2.43 (m, 1H), 2.2 (m, 1H), 1.96 (m, 1H), 1.45 (m, 2H), 1.15 (m, 2H), 0.79 (t, 3H).

Example 18
Compound GERI-AmE2=R(+)-N-[cyanomethyl][(5,6-dichloro-2,3,9,9a-tetrahydro-3-oxo-9a-propyl-1H-fluoren-7-yl)oxy]acetamide Compound [1] (370 mg, 1 mmol) was dissolved in dry THF (2 ml). CDI (200 mg, 1.2 mmol) and a solution containing aminoacetonitrile hydrochloride (200 mg, 2.2 mmol) and DIEA (2.2 mmol) in THF/$CH_2Cl_2$ were added. When TLC (using EtOAc solvent) indicated complete reaction, diethyl ether was added and the solution was washed with water. The organic phase was dried with magnesium sulfate, filtered, and evaporated. Recrystallization from EtOAc gave 230 mg (69% yield) of a white powder, with the structure named above and shown in FIG. 10, designated as GERI-AmE2. $^1$H-NMR (500 MHz, $CDCl_3$): δ=7.27 (bt, 1H), 6.83 (s, 1H), 6.80 (s, 1H), 4.66 (s, 2H), 4.33 (d, 2H), 3.03 (d, 1H), 2.76 (d, 1H), 2.55 (m, 2H), 2.3 (m, 1H), 2.0 (m, 1H), 1.5 (m, 2H), 1.2 (m, 2H), 0.86 (t, 3H).

Example 19

Synthesis of GERI-AmE3=R(+)-N-benzyl-[(5,6-dichloro-2,3,9,9a-tetrahydro-3-oxo-9a-propyl-1H-fluoren-7-yl)oxy]acetamide This compound was synthesized by dissolving compound [1] (240 mg, 0.65 mmol) in dry $CH_2Cl_2$ (2 ml). CDI (317 mg, 1.95 mmol) was added and the reaction was stirred for 10 minutes. Benzylamine (214 μl, 1.95 mmol) was added dropwise. When TLC (EtOAc/toluene 20:1) indicated the reaction was complete, dichloromethane was added and the solution was washed with water, 10% citric acid solution, and water again. The organic phase was dried with sodium sulfate, filtered, and evaporated. Silica gel chromatography (5% MeOH/$CH_2Cl_2$) was used to purify 265 mg (89% yield) of the product. $^1$H-NMR (500 MHz, $CDCl_3$): δ=7.3 (m, 5H), 7.11 (bt, 1H), 6.84 (s, 1H), 6.79 (s, 1H), 4.63 (s, 2H), 4.58 (m, 2H), 3.00 (d, 1H), 2.74 (d, 1H), 2.57 (ddd, 1H), 2.46 (dd, 1H), 2.27 (dd, 1H), 2.00 (ddd, 1H), 1.61 (ddd, 1H), 1.46 (ddd, 1H), 1.27 (m, 1H), 1.17 (m, 1H), 0.86 (t, 3H). MS m/z 458/460 (M+H)$^+$.

Example 20

Synthesis of GERI-AmE4=R(+)-N-[(2-pyridylmethyl)][5,6-dichloro-2,3,9,9a-tetrahydro-3-oxo-9a-propyl-1H-fluoren-7-yl)oxy]acetamide Starting reagent [1] (410 mg, 1.1 mmol) was dissolved in dry tetrahydrofuran (THF; 3 ml). Carbonyldiimidazole (CDI; 200 mg, 1.2 mmol) and 2-(aminomethyl)pyridine (125 μl, 1.2 mmol) were added. When TLC (10% MeOH/$CH_2Cl_2$) indicated complete reaction, ethyl acetate was added and the solution was washed with water. The organic phase was dried with magnesium sulfate, filtered, and evaporated. After recrystallization from MeOH/water, 350 mg (69%) of an off-white powder were obtained.

$^1$H-NMR (500 MHz, $CDCl_3$): δ=8.57 (d, 1H), 8.07 (bs, 1H), 7.69 (t, 1H), 7.24 (m, 1H), 6.87 (s, 1H), 6.81 (s, 1H), 4.68 (d, 2H), 4.66 (s, 2H), 3.02 (d, 1H), 2.76 (d, 1H), 2.58 (ddd, 1H), 2.48 (dd, 1H), 2.28 (dd, 1H), 2.01 (ddd, 1H), 1.61 (ddd, 1H), 1.47 (ddd, 1H), 1.29 (m, 1H), 1.19 (m, 1H), 0.86 (t, 3H).

Example 21

Synthesis of GERI-AmE5=R(+)-N-[3-(1-imidazolyl)-propyl][(5,6-dichloro-2,3,9,9a-tetrahydro-3-oxo-9a-propyl-1H-fluoren-7-yl)oxy]acetamide This compound was synthesized by dissolving compound [1] (0.5 g, 1.36 mmol) in dry THF (5 ml). CDI (235 mg, 1.4 mmol) and 1-(3-aminopropyl)imidazole (250 μl, 2 mmol) were added, and stirring was continued overnight at room temperature. When thin layer chromatography (TLC) using 10% MeOH in $CH_2Cl_2$ indicated complete reaction, toluene and 10% ethyl acetate were added to the reaction mixture. The reaction mixture was washed with water, the organic phase was dried with magnesium sulfate, filtered, and evaporated to give 442 mg of a slightly yellowish powder (66% yield). This compound was analyzed by nuclear magnetic resonance, and the results were as follows: $^1$H-NMR (500 MHz, $CDCl_3$): δ=7.44 (s, 1H), 6.99 (s, 1H), 6.88 (s, 1H), 6.80 (s, 1H), 6.72 (s, 1H), 4.49 (s, 2H), 3.97 (t, 2H), 3.35 (q, 2H), 2.96 (d, 1H), 2.78 (d, 1H), 2.57 (ddd, 1H), 2.47 (dd, 1H), 2.27 (dd, 1H), 2.01 (ddd, 1H), 1.61 (ddd, 1H), 1.48 (ddd, 1H), 1.3 (m, 1H), 1.2 (m, 1H), 0.79 (t, 3H).

Example 22

Synthesis of GERI-AmE6=R(+)-N-methyl-N-[(2-oxazolinyl)methyl][5,6-dichloro-2,3,9,9a-tetrahydro-3-oxo-9a-propyl-1H-fluoren-7-yl oxy]acetamide This compound is prepared by a 5-step process. The first step is carried out as described in Example 7, except that an equimolar amount of the ethyl ester of sarcosine is used instead of ethanolamine. The resulting compound is an ester where the 7-position substituent is $C_2H_5OOCCH_2N(CH_3)COCH_2O$—. This ester is hydrolyzed to the corresponding acid, which is then used in a reaction similar to the first step set forth in Example 7, to give the corresponding 2-hydroxyethylamide. Conducting the final two steps as described in Example 7 provides the desired product.

Example 23

Testing of D-Aspartate Release by Astrocytoma Cells

The in vitro tests described in this example used UC11-MG human astrocytoma cells, obtained from the University of Cincinnati, and described in Liwnicz et al 1986 and Lomneth et al 1989. Cell culture reagents (including RPMI 1640, fetal bovine serum, trypsin, and gentamicin) were obtained from Gibco (Gaithersburg, Md.). Radiolabelled D-[2,3-$^3$H]aspartate was obtained from Amersham Life Sciences (Buckinghamshire, England). ScintiVerse II scintillation fluid was obtained from Fisher Scientific (Pittsburgh, Pa.). All other chemicals were obtained from Sigma Chemical Co. (St. Louis, Mo.). Osmolarities of solutions were measured using the Advance DigiMatic Osmometer Model 3D II (Advanced Instruments Inc., Mass.).

The UC11-MG astrocytoma cells were cultured in 75 ml vented flasks at 37° C. inside a humidified incubator in 5% $CO_2$/95% air. The cells were grown in RPMI Medium 1640 supplemented with 10% fetal bovine serum and 200 mg/ml gentamicin. At approximately 90% confluence, the cells were detached and suspended using a 0.0625% trypsin solution in Buffer A (137 mM NaCl, 5.37 mM KCl, 5.55 mM glucose, 4.17 mM $NaHCO_3$, and 0.54 mM EDTA disodium salt, pH 7.4). The cells were then plated onto 6-well tissue culture plates at a seeding ratio of 4 plates per flask and 4 ml of cell-media suspension per well. The plated cells were used in experiments the next day at approximately 90% confluence. Plates that appeared to be more than 95% confluent were not used, because higher levels of confluence led to uncontrollable differentials in exposure of the cells to culture media and labelled aspartate. All tests were performed in triplicate. All media collections were done at 5 minute intervals, using pipettes, and were followed by promptly loading fresh buffer into each well before any drying occurred. All buffer samples collected in this manner were loaded into scintillation vials, mixed with 5 ml scintillation fluid, and counted for 1 minute in a scintillation counter (Beckman LS8000, Fullerton, Calif.).

Prior to D-aspartate exposure, the wells were washed three times under sterile conditions with 3 ml of 37° C. Buffer B (122 mM NaCl, 3.3 mM KCl, 1.2 mM $CaCl_2$, 0.4 mM $MgSO_4$, 1.2 mM $KH_2PO_4$, 25 mM Hepes, 10 mM glucose, pH 7.4). The osmolarity of Buffer B was approximately 285 mOsm; this is a normal ("iso-osmotic") level which does not cause swelling of the cells or release of aspartate by the cells.

The cells were then loaded with 0.5 µCi/ml of D-aspartate, and incubated at 37° C. for 30 min. Cells were then washed four times with Buffer B, and the last washing fluid was left on the cells. The plates were then placed on an orbital shaker and maintained at 37° C. This commenced the incubation period (time=0 minutes), as shown in FIG. 11.

Baseline aspartate release levels (prior to drug treatment) were determined by incubating the cells with normal Buffer B (285 mOsm) for 15 minutes, while buffer was collected every 5 minutes.

After the buffer was collected from a well at the 15 minute mark, the next set of normal Buffer B added to that well contained a test compound at a known concentration; each compound was tested over a range of concentrations. Cells were then incubated for two 5 minute intervals with solutions of test compounds in normal Buffer B. In some tests which used buffers containing relatively high concentrations of a test drug with limited solubility in water, DMSO was added to the mixture to increase the solubility of the compound in water. DMSO was also tested without any test drugs, and it was shown to have no effect on aspartate release.

Beginning at the 25-minute mark, the cells were stimulated to begin releasing aspartate by loading a well with hypo-osmotic buffer, prepared by diluting Buffer B with an equal volume of distilled and deionized $H_2O$, resulting in an osmolarity of about 145 mOsm. This hypo-osmotic solution caused the cells to begin taking in excess water, to try to reestablish the normal osmotic gradients that exist across the cell membranes. The water-induced swelling and stress then began to induce release of aspartate by the cells, and the amount of aspartate released by the swollen astrocyte cells was measured by removing the buffer every 5 minutes and testing it in a scintillation counter.

At the 35 minute mark, after 10 minutes of hypo-osmotic stress, normal Buffer B was added to the wells again, without any test drug, to commence a washing and recovery period. After 15 minutes of recovery, the cells were again subjected to hypo-osmotic stress using diluted Buffer B with no drug. This "second cycle" of osmotic stress confirmed three important factors: (i) that the cells were still viable and capable of secreting still more labelled aspartate, if stressed again; (ii) that the cells contained enough radiolabelled aspartate to secrete substantial quantities once again, if stressed; and (iii) to ensure that each test drug reacted with the cells in a reversible manner, and did not undergo a permanent binding reaction or cause a lasting alteration in the cells. Cells treated with all of the fluorenone compounds that were tested performed in the desired manner, and showed substantial second spikes during the second stress cycle.

After these measurements were completed, the cells were then washed for 20 minutes using isotonic Buffer B, causing neurotransmitter release to return to near baseline levels. The remaining radioactivity (i.e., the quantity of D-aspartate that remained inside the cells despite the entire treatment process) was extracted from the cells by lysing the cells with 1 ml of 2N NaOH. The wells were washed with an additional 1 ml of distilled and deionized $H_2O$, which was combined with the cell extract in a 7 ml scintillation vial, for counting.

The percent of D-aspartate that had been released at each 5 minute interval was calculated by dividing the radioactivity of each 5-minute sample, by the total radioactivity (measured for each well by adding the values from all samples plus the residual values after the cells had been lysed). This expresses the amount of neurotransmitter release as the percent of total radioactivity remaining in the cells at each time period (% fractional release). The data generated by any compound that was tested could be plotted on a graph in the manner shown in FIG. 11, to indicate aspartate release as a function of both time and drug concentration.

The concentration of test compound that inhibited neurotransmitter release by 50% (the $IC_{50}$ values, as shown in Table 1) was determined for each compound by a method that calculated the total area under the curve (AUC) for each of several concentrations, and analyzing the AUC values as a function of concentrations for each test compound.

The researchers who carried out those tests also determined, using light microscope examination of the confluent cell layers at various times during the tests, that fluorenone compounds which reduced aspartate release were also effective in significantly reducing the amount of swelling and edema that the cells appeared to suffer.

Example 24
In Vivo Tests of Global Cerebral Ischemia

In one set of in vivo tests, the bilateral carotid occlusion model in gerbils was used to evaluate the abilities of a selected compound, GERI-E7, to protect against neuronal damage caused by global brain ischemia. These tests were performed in the laboratory of Dr. Claude Wasterlain, at the Sepulveda Veterans Administration Medical Center, in Los Angeles, Calif.

Adult male Mongolian gerbils were subjected to reversible bilateral carotid occlusion for 5 minutes, according to standard methods (e.g., Wasterlain et al 1992 and 1996). Each gerbil in a test group was then treated with a test compound at either 2 or 20 mg/kg, dissolved in injectable saline and administered intravenously (IV). Control animals were treated with saline. All treatment and control groups had 10 animals per group. Body temperature was maintained throughout the procedure by a heat lamp and rectal probe.

The gerbils were sacrificed 72 hours after surgery, and their brains were perfusion-fixed with paraformaldehyde. Serial sections of the brain were cut and stained with hematoxylin and eosin, and quantitative cell counts of live and dead neurons were made, using light and fluorescence microscopy, in two different parts of the brain that are highly sensitive to ischemic damage: (i) the subiculum, a zone of transition between the parahippocampus and the hippocampus; and (ii) the CA1 portion of the hippocampus. Statistical analysis was performed on all damage scores (non-paired student t test). All evaluations were made using double-blinded methods.

Damage results which compare control and treated animals for damage in both brain regions are shown in FIG. 12. As indicated by those graphs, the GERI-E7 compound provided a substantial and statistically significant reduction in neuronal damage in both brain regions that were evaluated.

Neuronal damage in other brain regions was also evaluated, using mainly visual semi-quantitative methods. The results confirmed that the GERI-E7 compound provided significant reduction in neuronal damage levels in most of the other areas that were considered.

Example 25
In Vivo Tests of Focal Cerebral Ischemia

In a second set of in vivo tests, a middle cerebral artery occlusion model was used in rats, to evaluate the ability of test compound GERI-E7 to reduce neuronal damage caused by focal brain ischemia. These tests were also performed in the laboratory of Dr. Claude Wasterlain, at the Sepulveda VA Medical Center in Los Angeles.

Male Sprague-Dawley rats (220 to 285 g) were intubated with an 18 gauge gavage needle and artificially respirated with a Harvard small animal respirator, 50 to 60 strokes/min, 2.0 to 3.0 cc. Anesthetization was induced by administering 1 to 2% methoxyflurane in a 1:2 $O_2$:$N_2O$ gas mixture. To allow for rapid induction of the anesthetic state, succinyl-choline (4 mg/kg, i.p.) was given immediately after anesthesia commenced, and surgery began 15 to 20 minutes later. Body temperature was maintained throughout by a heat lamp and rectal probe.

Focal cerebral ischemia was induced by reversibly clipping the right middle cerebral artery (MCA) and the right common carotid artery (CCA), as described in articles such as Kaplan et al 1991. A tracheal incision approximately 2.5 cm long was made, allowing placement of 4-0 suture silk under the CCA. This allowed rapid manipulation of the artery for clip placement. The temporalis muscle was partially excised and a 2 mm burr hole was drilled 2–3 mm rostral to the point of fusion of the zygoma with the temporal bone. Saline was used throughout this procedure for washing and maintenance of moisture.

The MCA was occluded below the rhinal fissure with a Codman Microaneurysm Clip #1. After the MCA was occluded the animal was turned onto its back and the CCA was occluded with a Roboz Microaneurysm Clip RS-5424.

A moistened piece of cotton was placed on the head wound and the tracheal region was partially closed by suture prior to placement of the animal in a warm cage with an oxygen tent. After a two-hour occlusion period (shown to produce a consistently measurable but non-lethal infarct), the clips were removed and methoxyflurane was administered via a nose cone. Visual verification was made for both artery occlusion, and post-occlusion reperfusion.

After the clips were removed and reperfusion was established, each animal was treated with either the GERI-E7 compound, at 20 mg/kg IV, or with the saline vehicle. All test and control groups had 10 animals. The wounds were closed and the animals were returned to their home cages.

Animals were sacrificed 72 hours later, and the brains were perfusion-fixed with 4% paraformaldehyde. Serial sections of the brain were cut and stained with hematoxylin and eosin. Infarct area was measured with an image analysis system at 8 to 10 levels between the posterior hippocampus and piriform olfactory cortex, to the level of the rhinal fissure. Infarct volume was determined by multiplying the average infarct area by the length of the brain between the posterior hippocampus and the piriform olfactory cortex. Edema was estimated by subtracting the area of the left (ischemic) hemisphere from the right (non-ischemic) hemisphere. Infarct volume and edema values among groups were compared, using the non-paired Students t test.

The results of the infarct volume comparisons are shown in FIG. 13. These results indicated that the area of infarct volume was reduced by about 50%, by treatment with the GERI-E7 test compound. Edema was also reduced by treatment with the GERI-E7 test compound.

Thus, there has been shown and described new and useful compounds and methods for reducing neuronal damage following an injury or other insult to the brain and/or spinal cord. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Barron, K. D., et al, "Ultrastructural features of a brain injury model in cat: I. Vascular and neuroglial changes and the prevention of astroglial swelling by a fluorenyl (aryloxy) alkanoic acid derivative (L-644,711)," *Acta Neuropathol* 75: 295–307 (1988)

Bednar, M. M., et al, "In vitro evidence supporting two mechanisms of action for the anion transport inhibitor L-644,711 in cerebral ischaemia," *Neurol Res* 14: 53–6 (1992)

Bourke, R. S., "Swelling and ion uptake in cat cerebrocortical slices: control by neurotransmitters and ion transport mechanisms." *Neurochem Res* 8: 5–24 (1983)

Cragoe, E. J., "Agents for the treatment of brain edema 2: [(2,3,9,9a-Tetrahydro-3-oxo-9a-substituted-1H-fluoren-7-yl)oxy ]-alkanoic acids and some of their analogues," *J Med Chem* 29: 825–41 (1986)

Cragoe, E. J., "Drugs for the treatment of traumatic brain injury," *Medical Res Rev* 7: 271–305 (1987)

deSolms, S. J., et al, "(Acylaryloxy)acetic acid diuretics 2: (2-Alkyl-2-aryl-1-oxo-5-indanyloxy)acetic acids," *J Med Chem* 21: 437–43 (1978)

Kaplan, B., et al, "Temporal thresholds for neocortical infarction in rats subjected to reversible focal cerebral ischemia," *Stroke* 22: 1032–1039 (1991)

Kimelberg, H. K., et al, "Improved recovery from a traumatic-hypoxic brain injury in cats by intracisternal injection of an anion transport inhibitor," *Cent Nerv Syst Trauma* 4: 3–14 (1987)

Kimelberg, H. K., et al, "Astrocytic swelling in traumatic-hypoxic brain injury: Beneficial effects of an inhibitor of anion exchange transport and glutamate uptake in glial cells," *Mol Chem Neuropathol* 11: 1–31 (1989)

Kimelberg, H. K., et al, "Swelling-induced release of glutamate, aspartate, and taurine from astrocyte cultures," *J Neurosci* 10: 1583–1591 (1990)

Kohut, J. J., et al, "Reduction in ischemic brain injury in rabbits by the anion transport inhibitor L-644,711," *Stroke* 23: 93–97 (1992)

Liwnicz, B. H., et al, "Continuous human glioma-derived cell lines UC-11MG and UC-302MG," *J Neuro-Oncology* 3: 373–385 (1986)

Lomneth, R., et al, "Electrophysiological and biochemical characterization of a continuous human astrocytoma cell line with many properties of well-differentiated astrocytes," *Brain Research* 486: 95–107 (1989)

O'Connor, E. R., et al, "Electrical resistance method for measuring volume changes in monolayer cultures applied to primary astrocyte cultures," *Am J Physiology* 264 (*Cell Physiol* 33): C471–C478 (1993)

Trachtman H., et al, "Hyponatremia-induced brain edema in guinea pigs is reduced by treatment with the novel anion transport inhibitor L-644,711," *Life Sci* 45: 2141–7 (1989)

Wasterlain, C. G., et al, "Felbamate reduces hypoxicischemic brain damage in vivo," *Eur J Pharmacology* 212: 275–278 (1992)

Wasterlain, C. G., et al, "Felbamate protects CA1 neurons from apoptosis in a gerbil model of global ischemia," *Stroke* 27: 1236–40 (1996)

Woltersdorf, O. W., "(Acylaryloxy)acetic acid diuretics 1: (2-Alkyl- and 2,2-dialkyl-1-oxo-5-indanyloxy)acetic acids," *J Med Chem* 20: 1400–8 (1977)

What is claimed is:

1. A method of treating a human patient who is suffering or at risk of central nervous system damage, comprising the step of administering to the patient a pharmaceutical composition which contains a neuroprotective amount of a compound of the formula:

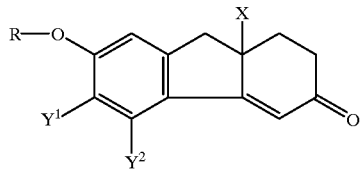

wherein X is selected from the group consisting of lower alkyl containing 1 to 3 carbon atoms; substituted lower alkyl; and lower cycloalkyl;

wherein R is a substituted alkyl group in which the substituents are selected from the group consisting of aryl and substituted aryl; and substituted or unsubstituted heterocyclic rings having 0 or 1 nitrogen atom and at least one double bond wherein the alkyl group is attached to a carbon atom of the heterocyclic ring; and wherein $Y^1$ and $Y^2$ are each selected from the group consisting of halogen, hydrogen, and methyl.

2. The method of treating a human patient of claim 1, wherein X is selected from the group consisting of propyl, hydroxyethyl, haloethyl, and cycloalkyl having less than 6 carbons.

3. The method of claim 1 wherein R is a heterocyclic-alkyl group.

4. The method of claim 3 wherein R is an oxazinyl-alkyl group.

5. The method according to claim 3 wherein the compound is selected from the group consisting of:

2-{[(5,6-dichloro-2,3,9,9a-tetrahydro-3-oxo-9a-propyl-1H-fluoren-7-yl)oxy]methyl}-tetrahydro-1,3-oxazine;

2-{[(5,6-dichloro-2,3,9,9a-tetrahydro-3-oxo-9a-propyl-1H-fluoren-7-yl)oxy]methyl}oxazoline;

2-{[(5,6-dichloro-2,3,9,9a-tetrahydro-3-oxo-9a-propyl-1H-fluoren-7-yl)oxy]methyl}thiazoline; and, enantiomers and pharmaceutically acceptable salts thereof.

6. The method of claim 3 wherein R is a pyridyl-alkyl group.

7. The method according to claim 6 wherein the compound is selected from the group consisting of:

5,6-dichloro-9a-propyl-7-(2-pyridylmethoxy)-2,3,9,9a-tetrahydro-1H-fluoren-3-one; and, 5,6-dichloro-9a-propyl-7-(3-pyridylmethoxy)-2,3,9,9a-tetrahydro-1H-fluoren-3-one; and, 5,6-dichloro-9a-propyl-7-(4-pyridylmethoxy)-2,3,9,9a-tetrahydro-1H-fluoren-3-one; and, enantiomers and pharmaceutically acceptable salts thereof.

8. The method according to claim 1 wherein R is a heterocyclicaralkyl group.

9. The method according to claim 8 wherein the compound is selected from the group consisting of:

5,6-dichloro-2,3,9,9a-tetrahydro-7-[4-(2-oxazolinyl)-phenylmethoxy]-9a-propyl-1H-fluoren-3-one; and, 5,6-dichloro-2,3,9,9a-tetrahydro-7-[3-(2-oxazolinyl)-phenylmethoxy]-9a-propyl-1H-fluoren-3-one; and, 5,6-dichloro-2,3,9,9a-tetrahydro-7-[2-(2-oxazolinyl)-phenylmethoxy]-9a-propyl-1H-fluoren-3-one; and, pharmaceutically acceptable salts thereof.

* * * * *